(12) United States Patent
Sumi et al.

(10) Patent No.: US 10,251,558 B2
(45) Date of Patent: Apr. 9, 2019

(54) METHOD AND APPARATUS FOR MEASURING AND DISPLAYING DENTAL PLAQUE, GINGIVA, AND ALVEOLAR BONE

(71) Applicant: National Center for Geriatrics and Gerontology, Obu-shi, Aichi (JP)

(72) Inventors: Yasunori Sumi, Obu (JP); Nobuyoshi Ozawa, Obu (JP); Yohei Gonda, Obu (JP)

(73) Assignee: National Center for Geriatrics and Gerontology, Obu-shi, Aichi (JP)

( * ) Notice: Subject to any disclaimer, the term of this patent is extended or adjusted under 35 U.S.C. 154(b) by 197 days.

(21) Appl. No.: 15/230,982

(22) Filed: Aug. 8, 2016

(65) Prior Publication Data

US 2016/0360969 A1 Dec. 15, 2016

Related U.S. Application Data

(62) Division of application No. 14/413,524, filed as application No. PCT/JP2013/069156 on Jul. 12, 2013, now Pat. No. 9,445,724.

(30) Foreign Application Priority Data

Jul. 19, 2012 (JP) .................................. 2012-160430

(51) Int. Cl.
*A61C 19/04* (2006.01)
*A61B 5/00* (2006.01)

(52) U.S. Cl.
CPC .......... *A61B 5/0088* (2013.01); *A61B 5/0066* (2013.01); *A61B 5/0086* (2013.01);
(Continued)

(58) Field of Classification Search
CPC ... A61B 5/0062; A61B 5/0066; A61B 5/0073; A61B 5/0088; A61C 9/0053
See application file for complete search history.

(56) References Cited

U.S. PATENT DOCUMENTS 5,570,182 A 10/1996 Nathel ................. A61B 5/0088
356/477
5,957,687 A 9/1999 Brilliant
(Continued)

FOREIGN PATENT DOCUMENTS

CN 101513366 A 8/2009
CN 101553161 A 10/2009
(Continued)

OTHER PUBLICATIONS

Communication pursuant to Article 94(3) EPC, EP Application No. 13 819 332.1, dated Jan. 24, 2018, 6 pp.
(Continued)

*Primary Examiner* — Ralph A Lewis
(74) *Attorney, Agent, or Firm* — Myers Bigel, P.A.

(57) ABSTRACT

A method and an apparatus for measuring and displaying dental plaque are provided, and the method includes the steps of dividing near infrared light output from a light source into measurement light and reference light, applying the measurement light toward a tooth in an oral cavity and scanning the tooth with the measurement light, producing interference light from reflected light and back-scattered light from the tooth and the reference light, generating an optical coherence tomographic image based on a scattering intensity value of the interference light, extracting a dental plaque region having a specific scattering intensity value from the optical coherence tomographic image, and quantifying the dental plaque. A method and an apparatus for measuring and displaying gingiva and/or alveolar bone are further provided. A method and an apparatus for quantifying dental plaque, digitizing the dental plaque, and generating an image of the dental plaque in a noncontact, noninvasive manner are thereby provided.

13 Claims, 13 Drawing Sheets

(52) U.S. Cl.
CPC ............ *A61B 5/4552* (2013.01); *A61C 19/04* (2013.01); *A61B 2576/02* (2013.01)

(56) References Cited

U.S. PATENT DOCUMENTS

| | | | |
|---|---|---|---|
| 6,179,611 B1 | 1/2001 | Everett | A61B 5/0088 433/29 |
| 6,522,407 B2 | 2/2003 | Everett | A61B 5/0073 356/364 |
| 7,184,150 B2 | 2/2007 | Quadling | A61B 5/0066 356/602 |
| 7,355,721 B2 | 4/2008 | Quadling | A61B 5/0066 356/479 |
| 7,796,243 B2 | 9/2010 | Choo-Smith | A61B 5/0066 356/72 |
| 7,823,782 B2 | 11/2010 | Yatagai | A61B 5/0062 235/454 |
| 8,270,689 B2 | 9/2012 | Liang | A61B 1/0638 382/128 |
| 8,345,257 B2 | 1/2013 | Bonnema | A61B 5/0062 356/479 |
| 9,445,724 B2 * | 9/2016 | Sumi | A61B 5/0066 |
| 2010/0296098 A1 | 11/2010 | Bonnema et al. | |

FOREIGN PATENT DOCUMENTS

| | | |
|---|---|---|
| CN | 101730498 A | 6/2010 |
| JP | 60-075409 | 4/1985 |
| JP | 2004-065994 | 3/2004 |
| JP | 2005-179188 | 7/2005 |
| JP | 2008-058138 | 3/2008 |
| JP | 2009-148337 | 7/2009 |
| JP | 2011-189078 | 9/2011 |
| JP | 2011-217973 | 11/2011 |
| WO | WO 2010/123892 A2 | 10/2010 |
| WO | WO 2011/114718 A1 | 9/2011 |

OTHER PUBLICATIONS

Carter et al. "Automated quantification of dental plaque accumulation using digital imaging", *J. of Dentistry* 32:623-628 2004.

Yeganeh et al. "Quantification of root surface plaque using a new 3-D laser scanning method", *J. Clin. Periodontol* 26:692-697 (1999).

International Search Report corresponding to International Application No. PCT/JP2013/069156 dated Aug. 13, 2013.

Chen et al., "Quantifying dental biofilm growth using cross-polarization optical coherence tomography," Letters in Applied Microbiology, 54, 2012, pp. 537-542.

Colston, Jr. et al., "Dental OCT," Optics Express, vol. 3, No. 6, Sep. 14, 1998, pp. 230-238.

Heidrich et al., "3D imaging of biofilms on implants by detection of scattered light with a scanning laser optical tomography," Biomedical Optics Express, vol. 2, No. 11, Nov. 1, 2011, pp. 2982-2994.

Extended European Search Report, European Patent Application No. 13819332.1, dated Mar. 21, 2016, 9 pages.

First Office Action, Chinese Patent Application No. 201380038362.3, Mar. 28, 2016, 8 pages.

\* cited by examiner (A)           (B)

(A)

(B)

METHOD AND APPARATUS FOR MEASURING AND DISPLAYING DENTAL PLAQUE, GINGIVA, AND ALVEOLAR BONE

RELATED APPLICATIONS

This application is a divisional application of pending U.S. patent application Ser. No. 14/413,524 filed Jan. 8, 2015, which is a 35 U.S.C. § 371 national stage application of PCT Application No. PCT/JP2013/069156, filed on Jul. 12, 2013, which claims priority from Japanese Application No. 2012-160430, filed on Jul. 19, 2012, the contents of which are incorporated herein by reference in their entireties. The above-referenced PCT International Application was published as International Publication No. WO 2014/013950A1 on Jan. 23, 2014.

TECHNICAL FIELD

The present invention relates to an apparatus and to a method for measuring and displaying dental plaque, gingiva, and/or alveolar bone. The present invention relates particularly not only to a dental plaque measurement/display apparatus and a dental plaque measurement/display method capable of displaying dental plaque present on a tooth surface including a surface of a tooth facing an adjacent tooth and an occlusal surface of a tooth, in an interdental space, in a gingival sulcus, and in a periodontal pocket in the form of two-dimensional and three-dimensional images and instantly calculating quantified values, such as the thickness, length, cross-sectional area, volume, and/or surface area of the dental plaque but also to a gingiva and/or alveolar bone measurement/display method and a gingiva and/or alveolar bone measurement/display apparatus capable of quantifying gingiva and/or alveolar bone to provide the amount of change in swelling of the gingiva and/or the amount of change in the alveolar bone.

BACKGROUND ART

In the dental clinical field, as a method for evaluating the presence of dental plaque attached to the surface of a tooth and the state of the dental plaque, dentists have primarily conducted visual inspection up until the present.

Since the color of dental plaque is white or translucent white, which is the same color as that of the surface of a tooth, it is difficult to recognize the attachment of the dental plaque on the surface of the tooth. In dental clinical practice, a dental plaque coloring method has been conventionally used. The dental plaque coloring method is a method using a plaque coloring solution, and in dental medical practice under insurance in Japan, Plaque Control Record (PCR method) developed by O'Leary has been introduced. With the PCR method, a tooth surface is divided into four portions, and the ratio of the number of portions to which dental plaque is attached to the total number of tooth surfaces is determined for evaluation of the state of oral cleanliness. The method is, however, a two-level evaluation method that simply evaluates presence or absence and hence fails to provide details of the state of dental plaque attachment. Further, the dental plaque coloring operation itself gives a patient strong discomfort, and removal of the coloring solution after the coloring operation is cumbersome.

Moreover, since portions other than dental plaque are also colored, the inspection method undesirably has low specificity and many other disadvantages. It cannot therefore be said that the PCR method is adequate to spread the recognition of the importance of oral cleaning.

As a method for evaluating dental plaque removal effects provided by a variety of brushing methods and motorized toothbrushes, the Loe-Silness dental plaque index is known. The method does not rely on coloring and cannot therefore clearly show the boundary among dental plaque, a tooth, and a periodontal tissue. The method provides the following four-level evaluation results: no dental plaque attachment; tactually recognized dental plaque; visually recognized dental plaque; and a large amount of dental plaque attachment. It cannot, however, be said that the method is a quantitative evaluation method because there are large differences among the four levels.

The dental plaque evaluation method among dental health evaluation methods provides scored results for seeming digitization and hence objectivity. The method, however, has problems of poor reproducibility and lack of true objectivity, that is, multiple inspection operators who execute the method cannot provide consistent values. It cannot therefore be said that the method is widely used in dental clinical practice. As an evaluation method based on dental plaque coloring, there is a known method described in PTL 1. The method is executed as follows: toothpaste to which 0.01 to 2.0 weight % of fluorescent dye is added is used to attach the fluorescent dye to dental plaque at a time of tooth brushing; light from an incandescent lamp or a fluorescent lamp is applied through an appropriate filter to the fluorescent dye to emit light from the fluorescent dye; and the amount of dental plaque is detected based on the amount of the emitted light.

PTL 2 also discloses a dental plaque coloring method. The method, however, has problems of bitterness of the coloring agent and low stability of the coloring agent when the coloring agent is stored. PTL 3 discloses a method using both a dye and light. The method is based in principle on the fact that the dye is excited by the light and emits fluorescent light, but the dye itself needs to strongly adhere to the dental plaque. Fluorescent dyes, such as chlorophyll and fluorescein, cannot also sufficiently dye dental plaque. Further, PTL 4 discloses a method for detecting dental plaque only by using specific light. The method, however, has a problem of inability to detect dental plaque formed in an initial stage.

In recent years, studies of methods for quantitatively evaluating dental plaque have advanced. For example, NPL 1 discloses a method for capturing an oral cavity photograph after dental plaque coloring in the form of a digital image and computationally calculating the area of the dental plaque in comparison with the surface of the tooth. The method, however, has difficulty in distinguishing the dental plaque from gingiva. Since an optical photograph captures an object only in a planar manner, front and rear sites in the photograph are likely to be evaluated differently. A dental plaque detection method based on a quantitative light-fluorescence method (QLF method: Quantitative light-fluorescence method) using light of a specific wavelength (370±40 nm) allows more characteristic visualization of dental plaque than surrounding tissues. The method therefore eliminates the need of dental plaque coloring, but captures the dental plaque only in a planar manner as in a typical optical photograph. In reality, no image processing software based on a typical optical photograph or an optical photograph using a specific wavelength has been brought into practice, and it can hardly be said that development of the image processing software is underway.

NPL 2 discloses a method for collecting impressions of dental plaque before and after removal thereof, performing digital three-dimensional scanning on a plaster cast of the tooth before and after the removal of the dental plaque, and stereoscopically evaluating the attachment of the dental plaque. The collection of impressions twice, i.e., before and after the removal of the dental plaque is, however, cumbersome, and practicability of the method is therefore very low in the clinical field. Further, the dental plaque measurement and evaluation based on the plaster cast is not realistic.

In recent years, an OCT apparatus for dental purposes has been developed and used to diagnose dental caries (PTL 5). PTL 5, however, only describes a method for measuring dental caries.

On the other hand, no noninvasive quantification of gingiva or alveolar bone has been reported.

CITATION LIST

Patent Literature

[PTL 1] Japanese Patent Application Publication No. 63-2528
[PTL 2] Japanese Patent Application Laid-Open No. 2005-179188
[PTL 3] U.S. Pat. No. 5,957,687
[PTL 4] Japanese Patent Application Laid-Open No. 2004-65994
[PTL 5] Japanese Patent Application Laid-Open No. 2008-058138

Non-Patent Literature

[NPL 1] Carter K, Landini G, Walmsley A D. Automated quantification of dental plaque accumulation using digital imaging. J Dent. 2004 Nov; 32(8): 623-8.
[NPL 2] Yeganeh S, Lynch E, Jovanovski V, Zou L. Quantification of root surface plaque using a new 3-D laser scanning method. J Clin Periodontol. 1999 Oct; 26(10): 692-7.

SUMMARY OF INVENTION

Technical Problem

Studies conducted so far have revealed that dental caries and periodontitis, which are two major dental diseases, result primarily from dental plaque. However, X-ray inspection (roentgen approach) used in typical dental clinical practice cannot generate images of dental plaque, and the fact that no effective method for inspecting dental plaque attachment has greatly prevented the diseases from be conquered. There is a demand for a method that replaces the dental plaque coloring method, a variety of evaluation methods based on scored dental plaque, and other methods having been conventionally used and is capable of quantitatively evaluating the thickness, cross-sectional area, and volume of dental plaque in an objective, noninvasive manner. Further, achievement of quantification of gingiva and/or alveolar bone, which is deeply related to development of periodontitis, is greatly significant in dental clinical practice.

The present invention has been made in view of these problems. That is, an object of the present invention is to provide a dental plaque measurement/display method and a dental plaque measurement/display apparatus capable of solving the problems of the conventional methods, executing a method for objectively evaluating dental plaque attachment including quantitatively measuring dental plaque in a noncontact, noninvasive manner, displaying a result of the measurement in the form of a two-dimensional or three-dimensional image, and calculating the thickness, length, cross-sectional area, surface area, and volume of the dental plaque with high reproducibility and no difference among results provided by various inspection operators. Another object of the present invention is to provide a gingiva and/or alveolar bone measurement/display method and a gingiva and/or alveolar bone measurement/display apparatus capable of quantitatively measuring not only dental plaque but also gingiva and alveolar bone, which are periodontia, in a noncontact, noninvasive manner, displaying a result of the measurement in the form of a two-dimensional or three-dimensional image, and providing the amount of change in the gingiva and alveolar bone.

Solution to Problem

An embodiment of the present invention relates to a method for measuring and displaying dental plaque including the steps of: dividing near infrared light output from a light source into measurement light and reference light; applying the measurement light toward a tooth in an oral cavity, and scanning the tooth with the measurement light; producing interference light from reflected light and backscattered light from the tooth and the reference light; generating an optical coherence tomographic image based on a scattering intensity value of the interference light; extracting a dental plaque region having a specific scattering intensity value from the optical coherence tomographic image; quantifying the dental plaque; and generating an image of the dental plaque. In the present specification, the "dental plaque" refers to a biofilm made, for example, of oral bacteria, mutan, insoluble glucan, and sugars that are substances that are actually attached on the surface of a tooth of interest. On the other hand, the "dental plaque region" refers to a region in the displayed optical coherence tomographic image in the method for measuring and displaying dental plaque according to the present invention, specifically, the region extracted as a portion representing dental plaque and displayed as dental plaque. From the same point of view, it is assumed that "gingiva" and "gingiva region," "alveolar bone" and "alveolar bone region," and "enamel" and "enamel region" are distinguished from each other.

The optical coherence tomographic image is preferably a two-dimensional optical coherence tomographic image that two-dimensionally displays the dental plaque region, an enamel region on which the dental plaque is attached, and a gingiva region distinguishably from one another.

The optical coherence tomographic image is instead preferably a three-dimensional optical coherence tomographic image that three-dimensionally displays, as a stereoscopic image, the dental plaque region, an enamel region on which the dental plaque is attached, and a gingiva region distinguishably from one another.

The optical coherence tomographic image is still instead preferably a combination of a two-dimensional optical coherence tomographic image that two-dimensionally displays the dental plaque region, an enamel region on which the dental plaque is attached, and a gingiva region distinguishably from one another and a three-dimensional optical coherence tomographic image that three-dimensionally displays, as a stereoscopic image, the dental plaque region, an enamel region on which the dental plaque is attached, and a gingiva region distinguishably from one another.

In the method, the step of quantifying the dental plaque preferably includes a step of digitizing a thickness and/or a length of the dental plaque based on the dental plaque region extracted from the two-dimensional optical coherence tomographic image.

In the method, the step of quantifying the dental plaque preferably includes a step of digitizing a volume of the dental plaque based on the dental plaque region extracted from the three-dimensional optical coherence tomographic image.

In the method, the step of quantifying the dental plaque preferably includes a step of digitizing a cross-sectional area of the dental plaque based on the dental plaque region extracted from the two-dimensional optical coherence tomographic image or the three-dimensional optical coherence tomographic image.

In the method, the step of quantifying the dental plaque preferably includes a step of digitizing a surface area of the dental plaque based on the dental plaque region extracted from the three-dimensional optical coherence tomographic image.

The method preferably further includes the steps of: creating a database containing at least one quantified value selected from a thickness of the dental plaque, a length of the dental plaque, a volume of the dental plaque, a cross-sectional area of the dental plaque, and a surface area of the dental plaque obtained in the step of quantifying the dental plaque; and displaying the quantified value in the time course in at least one form selected from an image, a table, and a graph.

The method preferably further includes the step of calculating an amount of change in the time course in at least one quantified value selected from the thickness of the dental plaque, the length of the dental plaque, the volume of the dental plaque, the cross-sectional area of the dental plaque, and the surface area of the dental plaque and displaying the calculated value in the time course in the form of a numerical value, a two-dimensional image, or a three-dimensional image.

Another aspect of the present invention relates to an apparatus for measuring and displaying dental plaque, the apparatus including a light source that outputs near infrared light; a splitter that divides the near infrared light into measurement light and reference light; a dental plaque measuring probe that applies the measurement light toward a tooth in an oral cavity, and that scans the tooth with the measurement light; a light receiving element that receives interference light produced from reflected light and back-scattered light from the tooth and the reference light; a computing section that converts a scattering intensity value of the interference light into a gray level value, and that generates an optical coherence tomographic image; an extraction/measurement section that extracts a dental plaque region, and that quantifies the plaque; and a display section that displays the optical coherence tomographic image and a result of the quantification.

Another aspect of the present invention also relates to software that causes a computer to execute a method for measuring and displaying dental plaque, the method including the steps of: generating an optical coherence tomographic image based on the scattering intensity of the interference light obtained by the method described in the previous section; extracting a dental plaque region based on the scattering intensity of the interference light; generating an image of the dental plaque region; and providing at least one quantified value selected from a thickness of the dental plaque, a length of the dental plaque, a volume of the dental plaque, a cross-sectional area of the dental plaque, and a surface area of the dental plaque based on the extracted dental plaque region.

In the software, before the step of extracting the dental plaque region, the method executed by the computer preferably further includes the step of morphologically identifying the dental plaque, gingiva, and enamel in the optical coherence tomographic image based on an anatomical fact.

The method executed by the computer preferably further includes the steps of: creating a database containing a value provided in the step of providing a quantified value; and displaying the quantified values in the time course in at least one form selected from an image, a table, and a graph.

A still another aspect of the present invention relates to a method for measuring and displaying gingiva and/or alveolar bone including the steps of: dividing near infrared light output from a light source into measurement light and reference light; applying the measurement light toward a tooth and periodontal tissue in an oral cavity, and scanning the tooth and the periodontal tissue with the measurement light; producing interference light from reflected light and back-scattered light from the tooth and the periodontal tissue and the reference light; generating an optical coherence tomographic image based on a scattering intensity value of the interference light; extracting a gingiva region and/or an alveolar bone region each having a specific scattering intensity value; quantifying the gingiva and/or the alveolar bone; generating and image of the gingiva and/or the alveolar bone. The method further includes the step of obtaining an amount of change in swelling of the gingiva and/or an amount of change in the alveolar bone by carrying out the step of quantifying gingiva and/or alveolar bone in the time course.

A still another aspect of the present invention relates to an apparatus for measuring and displaying gingiva and/or alveolar bone, the apparatus including a light source that outputs near infrared light; a splitter that divides the near infrared light into measurement light and reference, light; a measuring probe that applies the measurement light toward a tooth and periodontal tissue in an oral cavity, and that scans the tooth and the periodontal tissue with the measurement light; a light receiving element that receives interference light produced from reflected light and back-scattered light from the tooth and the periodontal tissue and the reference light; a computing section that converts a scattering intensity value of the interference light into a gray level value, and that generates an optical coherence tomographic image; an extraction/measurement section that extracts a gingiva region and/or an alveolar bone region, and that quantifies the gingiva and/or the alveolar bone; and a display section that displays the optical coherence tomographic image and a result of the quantification.

A still another aspect of the present invention relates to software that causes a computer to execute a method for measuring and displaying gingiva and/or alveolar bone, the method including the steps of: generating an optical coherence tomographic image based on the scattering intensity value of the interference light provided by the method described in the previous section; extracting a gingiva region and/or an alveolar bone region based on the scattering intensity value of the interference light; generating an image of the gingiva region and/or the alveolar bone region; quantifying the gingiva and/or the alveolar bone based on the extracted gingiva region and/or alveolar bone region; measuring an amount of change in swelling of the gingiva and/or an amount of change in the alveolar bone by carrying out the step of quantifying gingiva and/or alveolar bone in the time course.

Advantageous Effects of Invention

The methods and apparatus according to the present invention have the following features and provide an advantageous effect of encouraging more reliable dental practice.
[Objectivity and Universality]
In dental clinical practice and dental examination of related art, visual inspection, palpation, and other subjective inspection methods are primarily executed and results of the methods differ from each other. In contrast, the present invention can provide an evaluation method that objectively quantifies dental plaque, gingiva, and alveolar bone. The method and apparatus according to the present invention that automatically extract a dental plaque region in an image with no involvement of human evaluation by using a computer can acquire consistent data irrespective of inspection location and inspection operator, whereby the method and apparatus excel in reproducibility and can be used in a universal manner.
[Image generation and Digitization]
The method and apparatus according to the present invention can evaluate an entire layer of dental plaque, which cannot be detected with a dental image diagnosis apparatus based, for example, on X-rays, in the form of a two-dimensional image. In particular, the method and apparatus according to the present invention allow evaluation of a tomographic image and hence allow evaluation in the depth direction, whereby even dental plaque under a gingival cuff, which cannot be detected by visual inspection, can be detected. Further, dental plaque attachment can be evaluated based on a three-dimensional image of the dental plaque, whereby the thickness, length, cross-sectional area, surface area, and volume, of the dental plaque can be expressed in the form of an image and digitized. Even gingiva and alveolar bone, quantification of which has not been even attempted, can be quantified in the same manner.
[Quantification and Creation of Database]
The methods and apparatus according to the present invention, which allow quantitative measurement, provide high reproducibility and reliability. Further, the methods and apparatus according to the present invention allow measurement and evaluation in the time course. The capability of image generation and digitization allows the methods and apparatus according to the present invention to be used in dental examination, and results from the methods and apparatus can be provided in the form of a numerical database.
[Safety]
The methods and apparatus according to the present invention, which use near infrared light as observation light, allow inspection without medical exposure, which is inevitable in a dental x-ray method of related art. Further, since the methods and apparatus according to the present invention are based on a noncontact, noninvasive inspection method, inspection can be performed without damage to a structure of an attachment associated with periodontal tissue and without dissemination of bacteria into surrounding periodontal pockets.
[Reliability, High Sensitivity, and Specificity]
The near infrared light used in the methods and apparatus according to the present invention can pass through mutan, glucan, and other substances that form dental plaque and reach and visualize dentin. The methods according to the present invention, which can generate an image of an entire layer of dental plaque and distinguish specifically the dental plaque from the dentin, are high-sensitivity, high-specificity, highly reliable inspection methods.
[Effective in Informed Consent]
Since dental plaque has a color similar to that of a tooth surface, and dental caries, periodontitis, and other similar dental diseases do not cause a patient to sense initial subjective symptoms, insufficient early treatment has been a problem with these diseases. The methods and apparatus according to the present invention allow specifically positive quantification and evaluation of whether or not dental plaque is attached, whereby it can be expected to improve patient's motivation and conquer the diseases.

BRIEF DESCRIPTION OF DRAWINGS

FIGS. 3(A) and 3(B) also show the directions of X, Y and Z axes in the present specification.

FIGS. 13(A) and 13(B) diagrammatically show measurement of a cross-sectional area

FIG. 22(A) is a descriptive diagram for describing horizontal movement of a probe, and FIG. 22(B) is a descriptive diagram for describing vertical movement of the probe.

DESCRIPTION OF EMBODIMENTS

The present invention will be described below in detail with reference to the drawings. It is noted that the present invention is not limited to the following description.

[First Embodiment : Method and Apparatus for Measuring and Displaying Dental Plaque]

An embodiment of the present invention relates to an apparatus for measuring and displaying dental plaque. The apparatus for measuring and displaying dental plaque according to the present embodiment uses an OCT (optical coherent tomography) apparatus to selectively measure dental plaque, in particular. The OCT apparatus is capable of measuring an intravital tissue with very high microscopic resolution. Further, the OCT apparatus, which uses a light source that emits near infrared light, which can reach a site under a body surface, can perform measurement not only in a surface portion of a subject but also a deep portion under the body surface of the subject. Near infrared light, which is electromagnetic radiation having no detrimental effect on a living body, unlike roentgen-rays (X-rays), allows noninvasive inspection of a subject in an exact sense. The OCT apparatus in the present invention is, in particular, preferably a wavelength-swept OCT (swept source-OCT), which is a Fourier-domain OCT.

Figure 1:
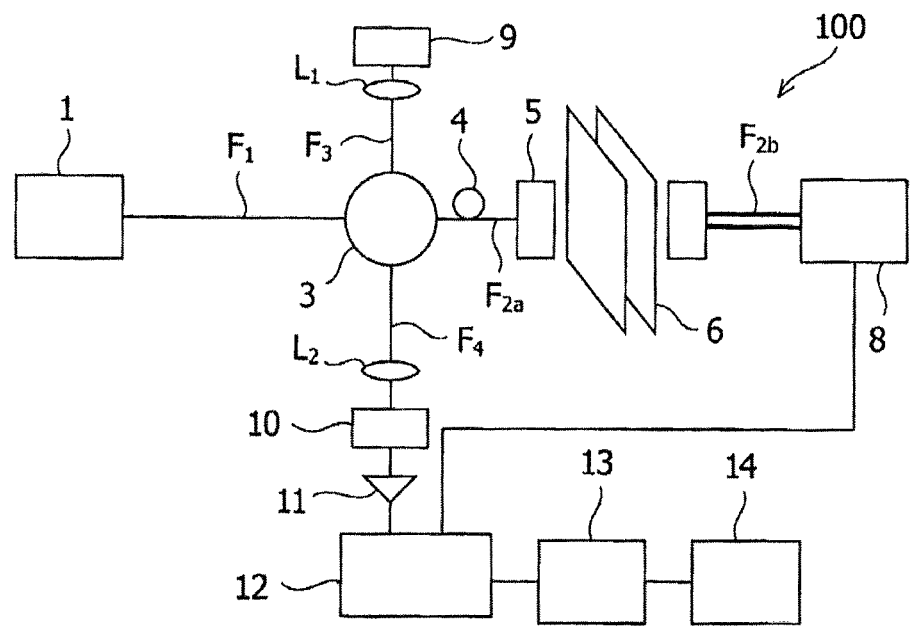
FIG. 1 is a block diagram showing an overall configuration of an apparatus for measuring and displaying dental plaque according to an embodiment of the invention.

FIG. 1 is a block diagram schematically showing the apparatus for measuring and displaying dental plaque according to the present embodiment. An apparatus for measuring and displaying dental plaque 100 shown in FIG. 1 substantially includes a near infrared light source 1, an optical interferometer unit that is constituted by a splitter 3, a collimator lens L1, a reference mirror 9, a plurality of optical fibers $F_1$, $F_2$, $F_3$, and $F_4$, and a rectifier 4, a dental plaque measuring probe 8, a light receiving element 10, a preamplifier (amplification device) 11, a computing section 12, a measuring section 13, and a display section 14.

In FIG. 1, the light source 1 is a wavelength-swept light source that generates an optical signal formed of light having a wavelength in a fixed range, for example, from 1310 to 1360 nm. The light source 1 is connected to the optical fiber $F_1$, and the optical fiber $F_1$ is connected to the splitter 3. One of the divided optical fibers after the splitter 3 or an optical fiber $F_{2a}$ is followed by the optical rectifier 4, an optical modifier 5, a polarizer, and an attenuation plate 6, in this order. The attenuation plate 6 is followed by the dental plaque measuring probe 8 with an optical fiber $F_{2b}$, which performs light transmission and light reception through a signal fiber, interposed therebetween. On the other hand, the optical fiber $F_3$, which is another one of the divided optical fibers after the splitter 3, is followed by the collimator lens L1 and the reference mirror 9. In addition to these components, an optical path adjustment section is provided in the configuration of the apparatus 100 in some cases in a position downstream of the optical fiber $F_{2a}$ and upstream of the optical fiber $F_3$.

The optical fiber $F_4$, which is another one of the divided optical fibers after the splitter 3, is followed by a photodiode that forms the light receiving element 10 via a collimator lens L2 interposed therebetween. A signal from the light receiving element 10 is amplified by the preamplifier 11 and then connected to the computing section 12 via an electric signal guiding wire. The computing section 12 is further connected to the measuring section 13 and the display section 14. The computing section 12 is further connected to a laser position sensor (not shown) in the probe 8.

The near infrared light source 1 emits near infrared light that belongs to a wavelength band that does not cause invasion of a living body. Specifically, the near infrared light source 1 is a laser light source that generates an optical signal formed of light having a single spectrum and can, for example, be a wavelength-swept fiber light source described in Japanese Patent Application Laid-Open No. 2006-80384. The laser oscillation wavelength preferably belongs, for example, to a 1.3-μm band, which is absorbed and scattered by water by a small amount. The range over which the wavelength is swept can, for example, be 100 to 200 nm, and the sweeping rate can, for example, be 20 kHz, but these values are not necessarily employed.

The splitter 3 only needs to be a component that can be connected to an optical fiber and can divide a light flux into light fluxes or combine light fluxes with each other at a desired ratio.

The light receiving element 10 is a device that converts interference light transmitted through the optical fiber $F_4$ into an electric signal. The light receiving element 10 is not limited to a photodiode and may, for example, be a balanced photodetector. The preamplifier 11 further amplifies the electric signal provided from the photodiode.

The computing section 12 and the measuring section 13 may be embodied by software installed in a computer and may not be separate sections but may be an integral section. The computing section 12 performs fast Fourier transformation on the electric signal from the preamplifier 11 to calculate data of a scattering intensity value and stores the data. The computing section 12 further stores data used to generate a three-dimensional image based on a position signal from the position sensor in the probe 8. The computing section 12 further converts the data of the scattering intensity value into data of a gray level value and stores data of the gray level value. The measuring section 13 extracts a dental plaque region from the data of the scattering intensity value and data of the gray level value. The measuring section 13 instead measures a specific length or distance based on data displayed in the form of an image and extracts the number of pixels or voxels.

The display section 14 may be a display device associated with a computer. The display section 14 displays a variety of images and calculated values provided from the measuring section 13.

Figure 2:
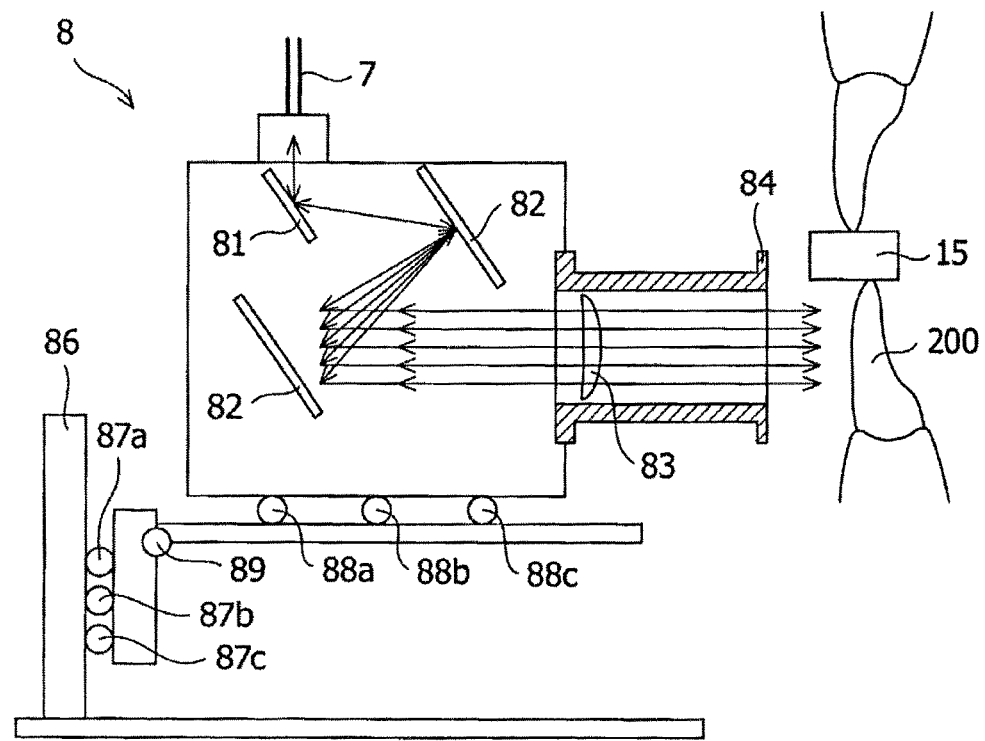
FIG. 2 is a schematic view showing the configuration of a dental plaque measuring probe portion.

The dental plaque measuring probe 8 is a portion that applies observation light directly to a subject and receives reflected light and back-scattered light. FIG. 2 is a schematic view showing the configuration of the dental plaque measuring probe 8. The dental plaque measuring probe 8 is primarily formed of a non-movable optical path control mirror 81, two movable optical path control mirrors 82, an objective lens 83, a dental plaque measuring probe front end portion 84, and an image capturing position adjustment stage 86. The image capturing position adjustment stage 86 is provided with an image capturing position adjustment X-axis controller 87a, an image capturing position adjustment Y-axis controller 87b, and an image capturing position adjustment Z-axis controller 87c and is configured to be capable of controlling the position of the dental plaque measuring probe with respect to a tooth or a subject. Similarly, the image capturing position adjustment stage 86 are provided with an image capturing position adjustment α-axis controller, an image capturing position adjustment β-axis controller 88b, and an image capturing position adjustment γ-axis controller 88c and is configured to be capable of controlling the position of the dental plaque measuring probe with respect to the tooth or the subject. These controllers can be electrically controlled by drivers (not shown). A control device (not shown) electrically connected to the drivers may be also configured to be operated by an operator. The probe 8 is further provided with the laser position sensor (not shown) that outputs a signal representing the relative position of the probe 8, and an output from the position sensor is supplied to the computing section 12.

The dental plaque measuring probe 8 shown in FIG. 2 is an example of a front tooth measuring probe, and a cheek tooth measuring probe, a dental Caries measuring probe, and other measuring probes can be detachably provided. These measuring probes can be switched from one to another in accordance with an intended purpose. The cheek tooth measuring probe has a probe front end portion where a reflection mirror capable of deflecting the observation light by 90 degrees is provided. The cheek tooth measuring probe can also be configured to include a mechanism that extends and retracts the probe front end for capturing an image of a tooth deviated from the tooth row. The range over which the probe front end can extend and retract is preferably about 10±10 mm. Further, the major diameter of the probe front end itself is preferably about 90±10 mm and the minor diameter thereof is preferably about 10±2 mm. The reason for this is that the thus set dimensions are anatomically effective. The plurality of types of detachable probe are described in detail in Japanese Patent Application Laid-Open No. 2011-189077.

Figure 17:
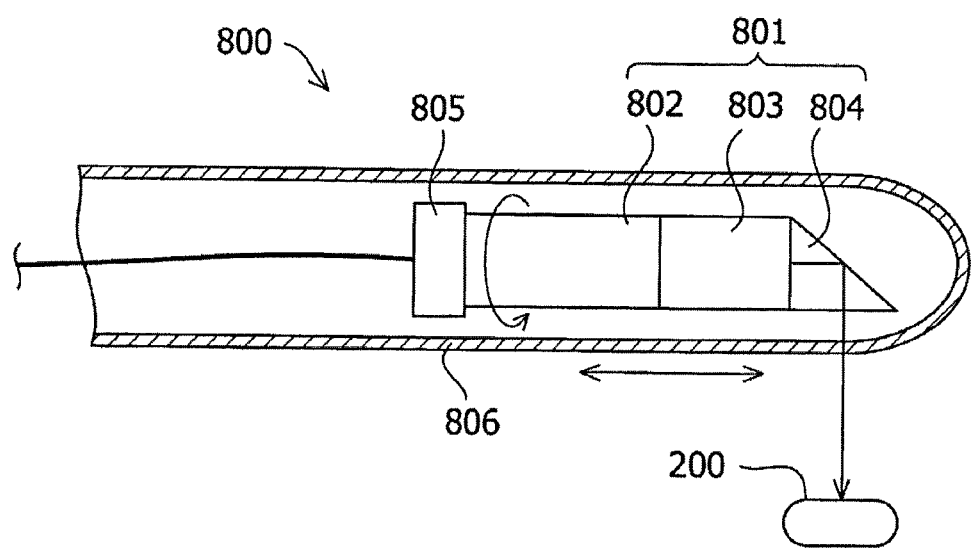
FIG. 17 is a descriptive diagram for describing a fiber-type probe preferably used to measure dental plaque on a tooth surface facing an adjacent tooth and a tooth occlusal surface.

FIG. 17 is a descriptive diagram for describing a fiber-type probe 800 preferably used to measure dental plaque on a surface of a tooth facing an adjacent tooth and/or an occlusal surface of a tooth. The dental plaque measuring fiber-type probe 800 has a sheath 806 and a probe body 801 disposed in the sheath 806, as shown in FIG. 17. The probe body 801 is connected to the front end surface of an optical fiber F with the axis of the probe body 801 aligned with the axis of the optical fiber F. The probe body 801 has a prism 804, a GRIN lens (gradient index lens) 803, and a connector/light guide 802, which connects the GRIN lens 803 to the optical fiber F, sequentially arranged from the front end side. The optical fiber F corresponds to the optical fiber $F_{2b}$ in FIG. 1. Furthermore, the prism 804 may, for example, be a rectangular prism and is so disposed that light guided through the optical fiber F exits out of the prism 804 at a right angle. The prism 804 may instead be so configured that the light guided through the optical fiber F exits out of the prism 804 at an acute angle, for example, 60 degrees, and is applied to a subject. The prism 804 may still instead be so configured that the light guided through the optical fiber F exits out of the prism 804 at an obtuse angle, for example, 130 degrees, and is applied to a subject. The thus configured prisms 804 may be configured to be attached to and detached from the probe body 801. The light deflected by the prism 804 passes through the sheath 806 and is applied to an object 200 of interest, which is present in a position outside the sheath 806.

In an embodiment, the sheath 806 may have matching oil for refractive index adjustment provided therein and filling the space between the sheath 806 and the probe body 801. The refractive index of the matching oil may be equal to or approximately equal to the refractive index of the prism 804 or may be equal to or approximately equal to the refractive index of the sheath 806. When the refractive index of the prism 804 is equal to or approximately equal to the refractive index of the sheath 806, the matching oil having the refractive index of equal to the refractive index of the prism 804 and the sheath 806 may be used. The matching oil that fills the sheath 806 preferably has a viscosity that roughly allows smooth rotation and frontward and rearward movement of the probe 800. Using matching oil for refractive index adjustment that fills the space between the sheath 806 and the probe body 801 prevents connection loss of light, whereby an image of a surface of a tooth facing an adjacent tooth and/or an occlusal surface of a tooth can be clearly captured.

The dental plaque measuring fiber-type probe 800 is provided with rotation means 805 at the proximal end of the probe body 801. The rotation means 805 preferably has an actuator including a motor, and the probe body 801 is connected to the rotary shaft of the motor. The probe body 801 can instead be rotated by human operation. Furthermore, the rotation means 805 is not necessarily disposed at the proximal end of the probe body 801, and a variety of changes are conceivable. Further, the direction of the rotation is diagrammatically indicated by the arrow in FIG. 2, but the direction of the rotation is not limited to that shown in FIG. 2. Moreover, the dental plaque measuring fiber-type probe 800 may be provided with movement means (not shown) disposed in the sheath 806 along the longitudinal direction thereof, and the movement means can be used to move the probe body 801 forward or rearward in the sheath 806. The forward or rearward movement can further widen the range over which dental plaque is imaged.

Figure 18:
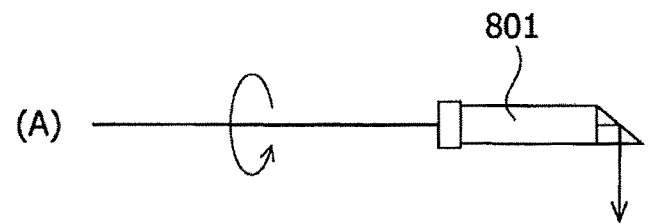
FIG. 18 is a diagrammatic view showing the rotation of a dental plaque measuring fiber-type probe and the range over which laser light is applied.

FIG. 18 is a diagrammatic view showing the rotation of the dental plaque measuring fiber-type probe 800 and the range over which light exits. FIG. 18(A) is a diagrammatic view showing the direction in which the light exits when the dental plaque measuring fiber-type probe is in a particular rotary position. FIG. 18(A) shows only the probe body 801 with the sheath omitted for ease of description. FIG. 18(B) is a diagrammatic view showing the direction in which the light exits when the dental plaque measuring fiber-type probe 800 is rotated by 360 degrees. Rotating the fiber-type probe 800 in use allows the light that exits out of the probe body 801 to be freely oriented over 360 degrees around the probe body 801. The thus configured dental plaque measuring fiber-type probe 800 allows realtime 360-degree tomographic imaging of freely chosen intravital tissue including dental plaque.

A tooth surface facing an adjacent tooth, which is one of the surfaces of teeth adjacent to and in contact with each other and has a very narrow area, is less frequently cleaned and self-cleaned than the other surfaces of the tooth. Dental plaque therefore tends to be attached to the tooth surface facing the adjacent tooth, which therefore tends to be a contaminated region and is believed to be one of the three sites most conducive to dental caries. The dental plaque coloring method, which is a gold-standard of dental plaque attachment evaluation method, cannot be applied to a tooth surface facing an adjacent tooth because it cannot be visually inspected. Books on cariology and conservative dentistry describe a conventional method for evaluating dental caries on a tooth surface facing an adjacent tooth, specifically, a method for inserting a tool into the space between teeth to separate the teeth from each other to allow direct inspection of the adjacent tooth surface. The method has, however, hardly been used because the method requires a long period to separate teeth and causes pain or discomfort. There is therefore a demand for a method for evaluating dental plaque attachment on a tooth surface facing an adjacent tooth, which is one of the three dental caries favorite sites, and it can be said that a tooth surface facing an adjacent tooth is a site where the quantitative dental plaque measurement according to the present embodiment is effectively used. Further, a large amount of dental plaque attachment on an occlusal surface of a cheek tooth, and the dental plaque attachment on the tooth occlusal surface primarily causes dental caries thereof. Using the dental plaque measuring fiber-type probe 800 shown in FIGS. 17 and 18 allows measurement of dental plaque on a tooth surface facing an adjacent tooth and/or dental plaque on a tooth occlusal surface, which cannot be quantitatively evaluated with technologies of related art.

A fiber-type probe developed by the present inventors and used to measure dental caries on a tooth surface facing an adjacent tooth is disclosed in Japanese Patent Application Laid-Open No. 2011-189078, and a fiber-type probe developed by the present inventors and used to measure dental caries on a tooth occlusal surface is disclosed in Japanese Patent Application Laid-Open No. 2011-217973. An OCT probe for measuring dental caries can also be used to measure dental plaque on a tooth surface facing an adjacent tooth and dental plaque on a tooth occlusal surface.

The present embodiment will next he described from a viewpoint of a measurement method with reference to FIG. 1. In FIG. 1, the light source 1 emits near infrared light that belongs to a wavelength band that does not cause invasion of a living body, for example, a wavelength band around 1300 nm. The light transmitted through the optical fiber $F_1$ is divided by the splitter 3 into reference light and observation light. The divided observation light is transmitted through the optical fiber $F_{2a}$ via the optical rectifier 4 and reaches the polarizer, the attenuation plate 6, and other components in the optical modifier 5, where the observation light is polarized and attenuated. As a result of the polarization and attenuation, the light having an aligned wave axis is transmitted through the optical fiber $F_{2b}$, which performs light transmission and light reception through a signal fiber, to the dental plaque measuring probe 8. The, light having been transmitted to the dental plaque measuring probe 8 undergoes optical path control at the non-movable optical path control minor 81 and the movable optical path control mirrors 822, each of which is, for example, a galvanometric mirror or a MEMS mirror, in the probe shown in FIG. 2 and moves in a raster pattern. The light moving in the raster pattern is focused by the objective lens 83, passes through the dental plaque measuring probe front portion 84, and reaches various portions of a tooth or a subject 200 as observation light. The various portions of the tooth include dental plaque, enamel, and dentin and even gingiva and alveolar bone of the periodontal tissue depending on the region to be imaged.

FIG. 3(A) is a conceptual diagram of the dental plaque measuring probe 8 and the subject 200 viewed from above the probe in FIG. 2. For ease of description, the direction of observation light 302 traveling through the tooth surface of the subject 200 toward the interior of the tooth is called a Z axis in the depth direction. FIG. 3(B) is a conceptual diagram of the probe viewed from a position in front thereof. An image of the tooth or the subject 200 is so captured that the tooth falls within a field of view 301, which is indicated by a phantom line.

For ease of description, X and Y axes are so defined that they are perpendicular to the direction of the observation light 302, which travels through the plane of view from the rear side thereof toward the front side thereof.

Figure 4:
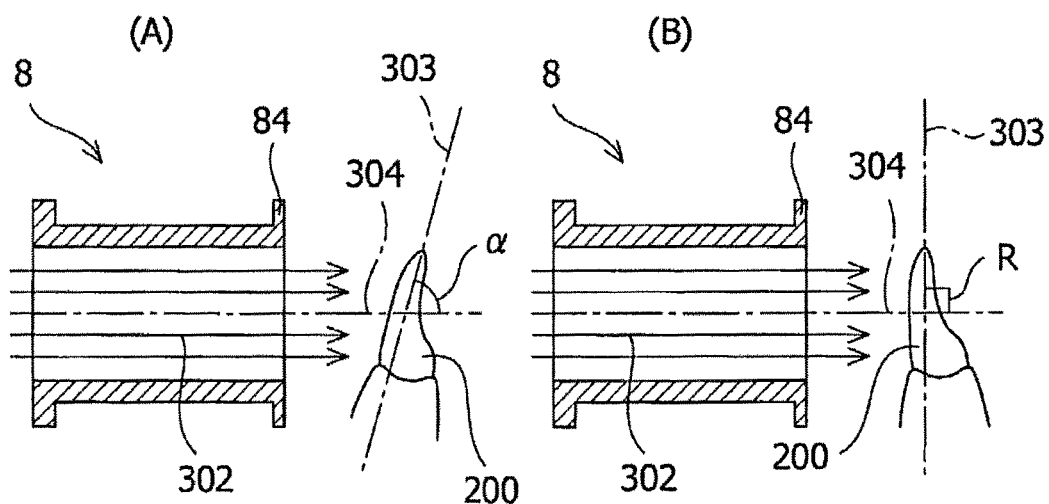
FIG. 4(A) is a schematic view in a case in which the angle between the tooth axis of a tooth or a subject and observation light incident on the tooth is inappropriate when the dental plaque measuring probe is viewed sideways.
FIG. 4(B) is a schematic view in a case in which the angle between tooth axis of the tooth and the observation light incident on the tooth is appropriate.
Figure 5:
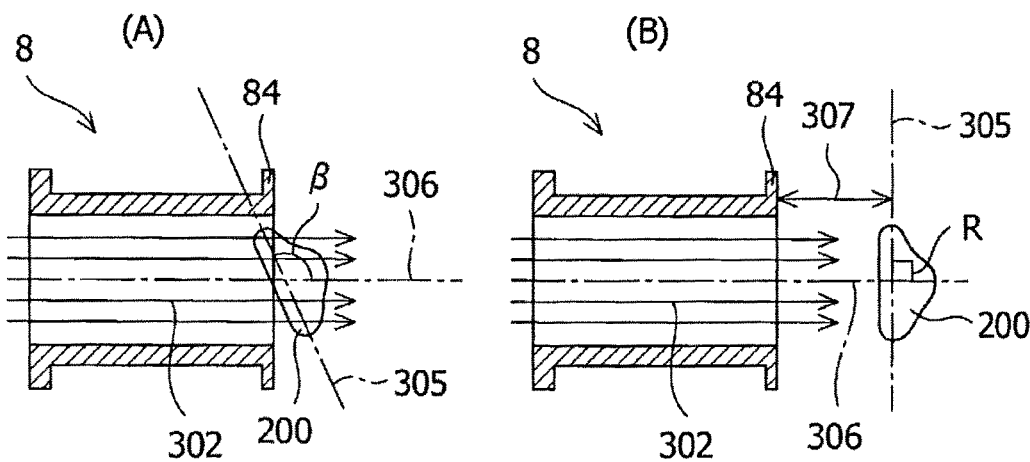
FIG. 5(A) is a schematic view in a case in which the angle between the tooth surface of a tooth or a subject to be imaged and observation light incident on the tooth and the distance between the dental plaque measuring probe and the subject are inappropriate when the dental plaque measuring probe is viewed from above.
FIG. 5(B) is a schematic view in a case in which the angle between the tooth surface of the tooth to be imaged and the observation light incident on the tooth and the distance between the dental plaque measuring probe and the subject are appropriate.
Figure 6:
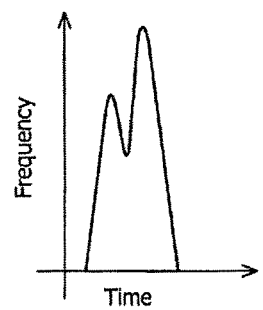
FIG. 6 shows a graph illustrating a time-and-frequency-axis relationship obtained in an electric signal conversion process carried out by a light receiving element.

FIG. 4(A) shows measurement made with an inappropriate angle between a tooth axis 303 of the subject 200 and the observation light 302 is, and FIG. 4(B) shows measurement made with an appropriate angle therebetween. When the angle α between an axis 304 parallel to the observation light 302 and the tooth axis 303 is close to R (90degrees), the angle between the subject 200 and the observation light 302 is appropriate. The angle α is preferably set at a value ranging from 85 to 95 degrees. FIG. 5(A) shows measurement made with an inappropriate angle between an axis 305, which is parallel to the tooth surface of the subject 200, and the observation light 302 and an inappropriate distance between the subject 200 and the probe 8. FIG. 5(B) shows measurement made with an appropriate angle between the axis 305, which is parallel to the tooth surface of the subject 200, and an axis 306, which is parallel to the observation light 302, and an appropriate distance 307 between the subject 200 and the probe 8. When an angle β between the axis 304, which is parallel to the observation light 302, and the axis 305, which is parallel to the tooth surface, is close to R (90 degrees), the angle between the subject 200 and the axis 306, which is parallel to the observation light 302, is appropriate. The angle β is also preferably set at a value ranging from 85 to 95 degrees. The distance 307 between the subject 200 and the probe 8 is preferably set at a value ranging from 1 to 5 mm.

A description will next be made of measurement of the subject 200 made by using the dental plaque measuring fiber-type probe 800. The dental plaque measuring fiber-type probe 800 can be advantageously used particularly when dental plaque on a tooth surface facing an adjacent tooth and a tooth occlusal surface is measured.

Figure 19:
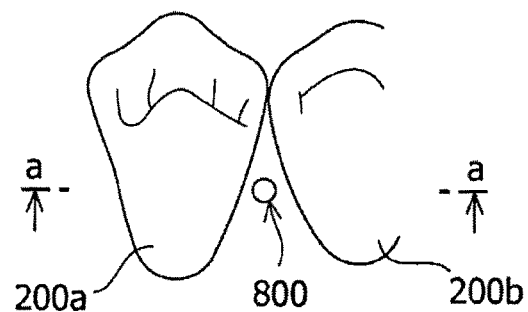
FIG. 19 is a descriptive diagram for describing a method for capturing an image of a tooth surface facing an adjacent tooth from the cheek side.
Figure 20:
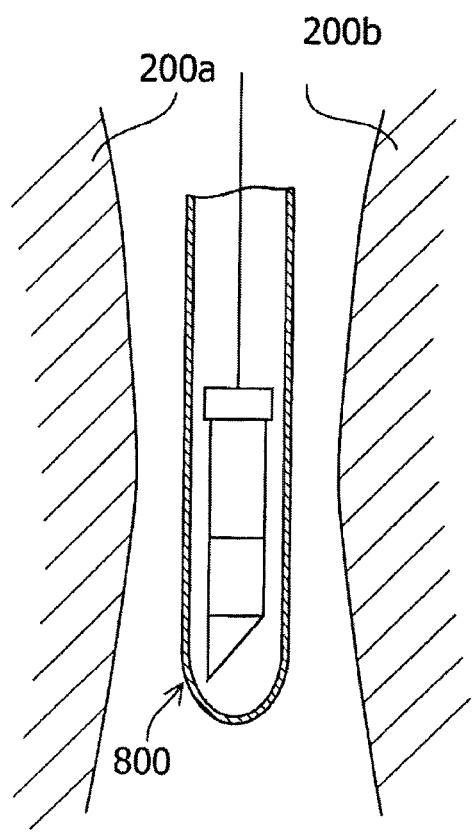
FIG. 20 is a cross-sectional taken along the line a-a in FIG. 19 and a descriptive diagram for describing the method for capturing an image of a tooth surface facing an adjacent tooth.

FIG. 19 is a descriptive diagram for describing a method according to the present embodiment for capturing an image of a tooth surface facing an adjacent tooth from the cheek side. FIG. 20 is a cross-sectional view taken along the line a-a in FIG. 19. As shown in FIG. 19, the dental plaque measuring fiber-type probe 800 is inserted into an upper or lower portion of an intertooth hourglass-shaped space, and the sheath 806 is fixed in the intertooth hourglass-shaped space into which the probe 800 has been inserted. At this point, the dental plaque measuring fiber-type probe 800, which is present in a position between a tooth 200a and another tooth 200b, can directly capture an image of a tooth surface facing the adjacent tooth, as shown in FIG. 20. Since the sheath 806 is flexible, the dental plaque measuring fiber-type probe 800 can be readily inserted into the intertooth hourglass-shaped space, but periodontal tissue in the vicinity of the intertooth hourglass-shaped space is unlikely to be damaged. The dental plaque measuring fiber-type probe 800 is then used to capture images of the tooth surface facing the adjacent tooth while the rotation means 805 is used to rotate the probe body 131. Instead, the dental plaque measuring fiber-type probe 800 is used to capture images of the tooth surface facing the adjacent tooth while the movement means (not shown) is used to move the probe body 801 forward or rearward in the fixed sheath 806. Still instead, the dental plaque measuring fiber-type probe 800 is used to capture images of the tooth surface facing the adjacent tooth while the rotation means 805 is used to rotate the probe body 801 and the movement means (not shown) is used to move the probe body 801 forward or rearward in the fixed sheath 806.

The probe body 801 is rotated, but not necessarily, by 360 degrees. For example, when the dental plaque measuring fiber-type probe 800 is inserted into an upper portion of the intertooth hourglass-shaped space, the probe body 801 can be rotated by lower-half 180 degrees, whereas, for example, when the dental plaque measuring fiber-type probe 800 is inserted into a lower portion of the intertooth hourglass-shaped space, the probe body 801 can be rotated by upper-half 180 degrees. Further, the sheath 806 may not be fixed in the intertooth hourglass-shaped space, and the dental plaque measuring fiber-type probe 800 can be used to capture images of a tooth surface facing an adjacent tooth while the probe body 801 along with the sheath 806 is moved forward or rearward. In this case, sheath movement means for moving the sheath 806 can replace the movement means for moving the probe body 801 forward and rearward in the sheath 806. Further, the sheath 806 may be configured to have a dual structure formed of an outer sheath and an inner sheath. In this case, the outer sheath is fixed in the intertooth hourglass-shaped space, and images of a tooth surface facing an adjacent tooth can be captured while the probe body 801 along with the inner sheath is moved frontward or rearward.

Figure 21:
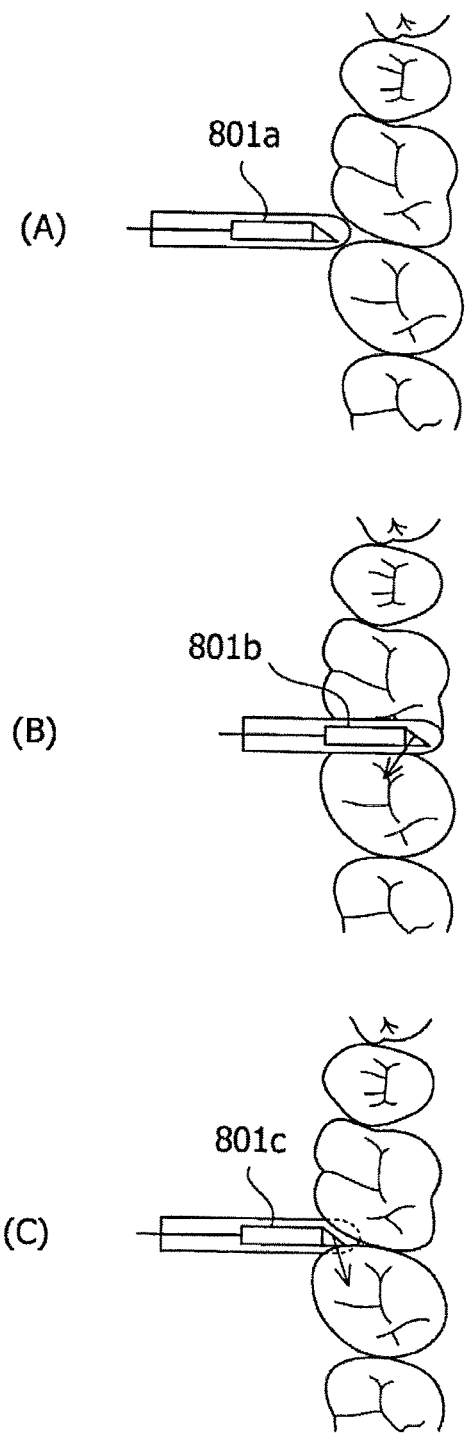
FIG. 21 is a descriptive diagram for describing a method for capturing an image of a tooth surface facing an adjacent tooth from the occlusal surface side.

FIG. 21 describes how to use the dental plaque measuring fiber-type probe 800 in another manner. FIG. 21(A) shows how to use the dental plaque measuring fiber-type probe 800 having a first probe body 801a including a prism configured to cause the light to exit out of the prism at a right angle. FIG. 21(B) shows how to use the dental plaque measuring fiber-type probe 800 having a second probe body 801b including a prism configured to cause the light to exit at an acute angle. FIG. 21(C) shows how to use the dental plaque measuring fiber-type probe 800 having a third probe body 801c including a prism configured to cause the light to exit at an obtuse angle. In an embodiment, the different probe bodies including the prisms that cause the light to exit at the different angles may be formed of the three types of probe body described in the previous section, and these probe bodies can be used interchangeably. That is, in typical usage, the first probe body 801a is used, as shown in FIG. 21(A). To insert the dental plaque measuring fiber-type probe 800 deep into the intertooth hourglass-shaped space and capture an image of a tooth surface facing an adjacent tooth from the deep position, the second probe body 801b is used, as shown in FIG. 21(B). When the intertooth hourglass-shaped space has a narrow lower portion and it is therefore difficult to insert the dental plaque measuring fiber-type probe 800, the third probe body 801c is used, as shown in FIG. 21(C). Therefore, even when the intertooth hourglass-shaped space has a narrow lower portion, and it is therefore difficult to insert the dental plaque measuring fiber-type probe 800, using an appropriate one of the plurality of probe bodies in accordance with an intended purpose allows an image of a tooth surface facing an adjacent tooth to be properly captured.

Figure 22:
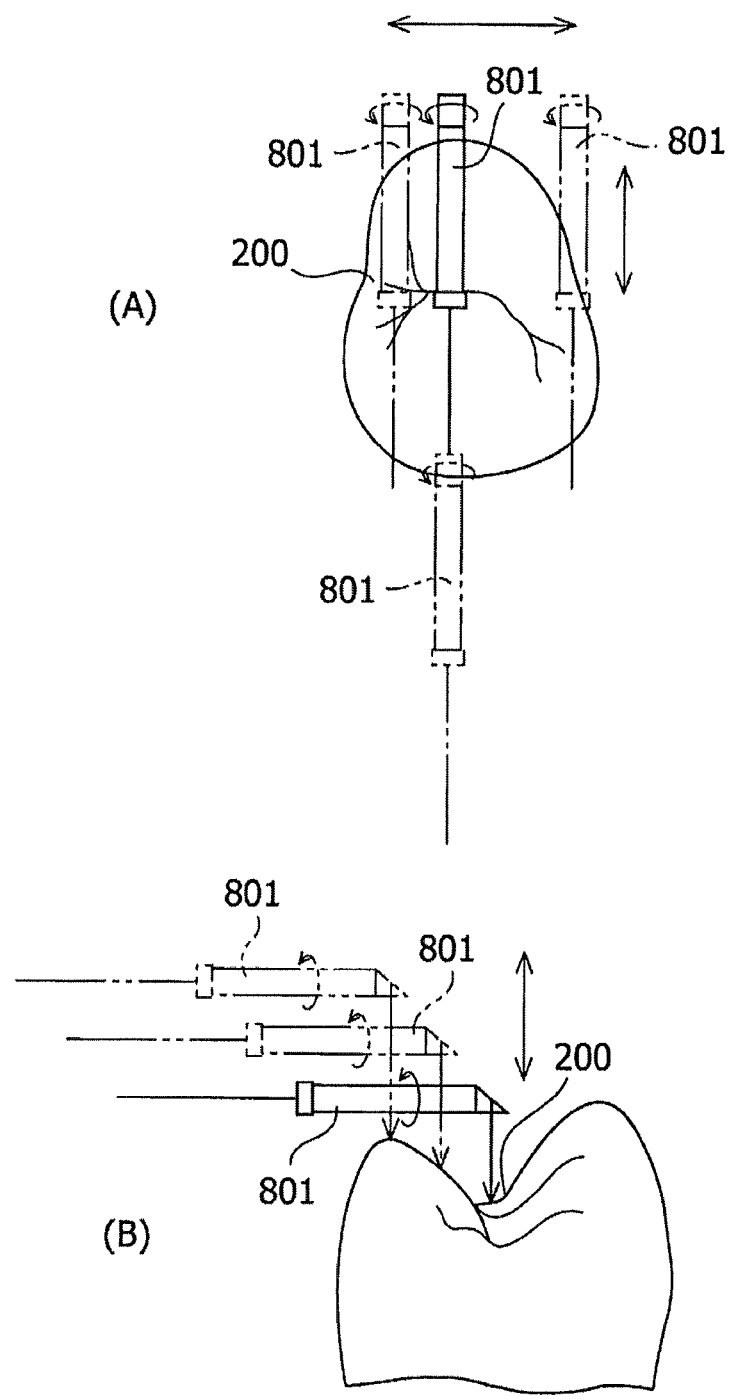
FIG. 22 shows a method for capturing an image of dental plaque on an occlusal surface of a tooth.

Next, FIG. 22 is a descriptive diagram for describing a method for capturing an image of an occlusal surface of a tooth by using the dental plaque measuring fiber-type probe 800. FIG. 22(A) describes the movement of the dental plaque measuring fiber-type probe 800 in the direction parallel to the occlusal surface, and FIG. 22(B) describes the movement of the dental plaque measuring fiber-type probe 800 in the direction perpendicular to the occlusal surface. To avoid complexity of the figures, the sheath 806 and the rotation means 805 are omitted in FIG. 22. The dental plaque measuring fiber-type probe 800 is disposed in a position in the vicinity of the occlusal surface of a tooth. The sheath 806, which is flexible, is unlikely to damage periodontal tissue. The movement means 805 is then used to move the probe body 801 forward or rearward in the sheath 806 while the rotation means 805 is used to rotate the probe body 801. The angular range over which the probe body 801 is rotated needs to allow images of the overall shape of the occlusal surface of the tooth to be captured when the probe body 801 is rotated. The angular range is not limited to a specific range and is, for example, from 30 to 90 degrees. It is noted that the probe body 801 is not moved forward or rearward but is only rotated to allow the dental plaque measuring fiber-type probe 800 to capture an image of dental plaque or the probe body 801 is not rotated but is only moved forward or rearward to allow the dental plaque measuring fiber-type probe 800 to capture an image of dental plaque. In some cases, horizontal movement means (not shown) can be used to move the dental plaque measuring fiber-type probe 800 horizontally (forward and rearward, rightward and leftward) for OCT image capturing according the shape of the occlusal surface of the tooth along the horizontal plane, as shown in FIG. 22(A). Further, in other cases, vertical movement means (not shown) is used to move the dental plaque measuring fiber-type probe 800 vertically (upward or downward) in such a way that the distance between the probe 800 and the object 200 under observation is kept constant for OCT image capturing according the shape of the occlusal surface of the tooth with high sensitivity and resolution, as shown in FIG. 22(B).

The observation light having exited out of the dental plaque measuring probe 8 or the dental plaque measuring fiber-type probe 800 according to a specific embodiment and having reached a subject thus undergoes optical physical phenomena, such as optical reflection, scattering, and absorption. Reflected light and back-scattered light that return along the same axis pass through the light receiving portion of the optical fiber $F_{2b}$ and optical rectifier 4 and return to the splitter 3.

On the other hand, the divided reference light from the splitter 3 is transmitted through the optical fiber $F_3$, is reflected off the reference mirror 9, and returns through the optical fiber $F_3$ to the splitter 3.

Figure 8:
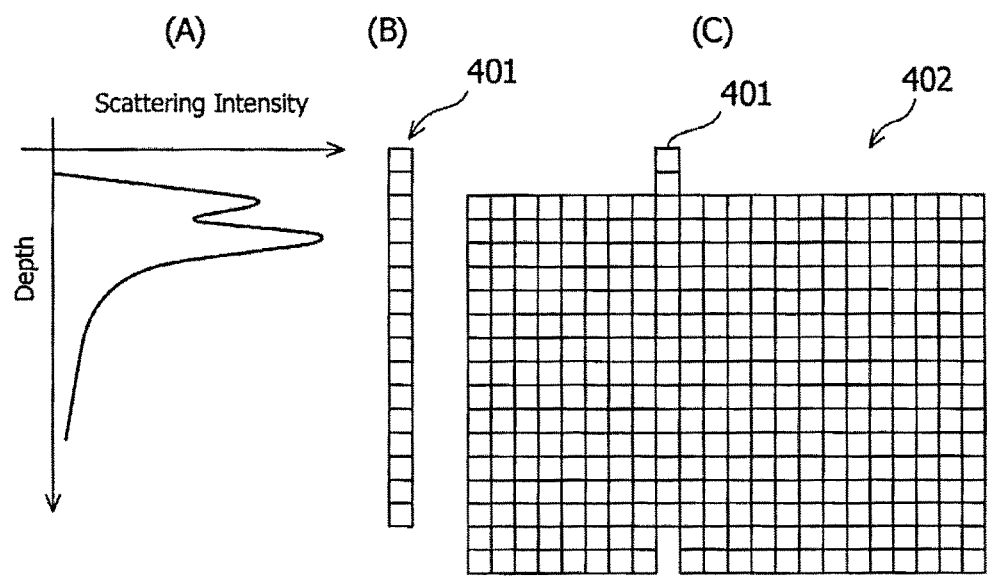
FIG. 8(A) shows a graph illustrating the relationship between the depth distance and the scattering intensity after fast Fourier transform.
FIG. 8(B) shows a matrix formed of a single column containing values of the depth distance and the scattering intensity.
FIG. 8(C) is a matrix formed of rows and columns created by profiling the matrix in (B).

The observation light and the reference light undergo an interference phenomenon, which is an optical physical phenomenon, and form interference light in the splitter 3. The interference light is collected by the collimator lens L2 and converted by the light receiving element 10 into an electric signal along the temporal axis based on a photoelectric effect. FIG. 8 shows a graph schematically illustrating a time-to-frequency relationship obtained when the interference light is converted by the light receiving element 10 into an electric signal. The horizontal axis represents time and the vertical axis represents frequency.

Figure 7:
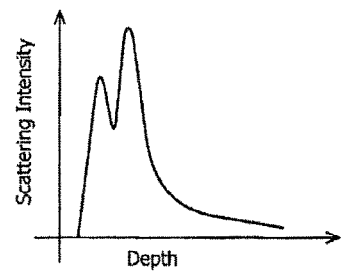
FIG. 7 shows a graph illustrating the relationship between a depth distance and a scattering intensity after fast Fourier transform.

The electric signal is transmitted via the electric signal guiding wire to the computing section 12. In the computing section 12, an interference electric signal resulting from the interference light and processed by the preamplifier 11 is synchronized with a timing signal and undergoes fast Fourier transform, which profiles a depth-direction signal. The interference signal is thus converted into scattering intensity values. FIG. 7 is a graph schematically illustrating the relationship between depth distance and scattering intensity axes obtained by the Fourier transform. The depth distance is a distance along the Z axis in FIG. 3(A) measured from the surface of a subject or an origin toward the direction in which the observation light travels. The scattering intensity values are stored in the computing section 12, for example, in the form of a float data that is a 4-byte single-precision floating-point real number (having 7 significant digits).

The resultant float data is then converted into 8-bit gray scale of a 256-level for visualization of the scattering intensity values. The gray scale can be configured to have 256gray level values of a range from 0 to 255. In the present invention, the 256 gray levels are not necessarily employed, and the present invention can be implemented based on any other number of gray levels. The conversion of the float data into gray level values can be performed by using commercial software, for example, Labview (manufactured by National Instruments Corporation), but other software can be used. The scale based on which the float data is converted into gray level values can be freely set by a person skilled in the art. In accordance with the set scale, color tone and contrast and hence a resultant image may change in some cases. A person skilled in the art can set the scale in accordance with an intended purpose. The thus obtained gray level value data can also be stored in the computing section 12.

To generate a two-dimensional optical coherence tomographic image displayed in multiple colors, a color scale is used in the process of converting scattering intensity values into gray level values. A color image can thus be generated in the same manner.

FIG. 8 schematically shows a process of profiling waveform data and converting the profiled waveform data into a computational matrix. The numerical relationship obtained by the Fourier transform (A) is stored in the form of a column 401 containing 16 pixels per column (B). It is noted that the description will be made of a case in which a single column contains 16 pixels for ease of description but an actual number of pixels per column preferably ranges from about 500 to 800. Gray level values ranging from 0 to 255 are then assigned to each of the pixels. Gray level values corresponding to scattering intensities at various depth distances along the Z axis, that is, gray level values at various depths in graph (A) are assigned to the pixels in (B). The assignment step is also applied to the following waveforms and the results are sequentially arranged to complete a matrix 402 (C), based on which a tomographic image is generated.

Figure 9:
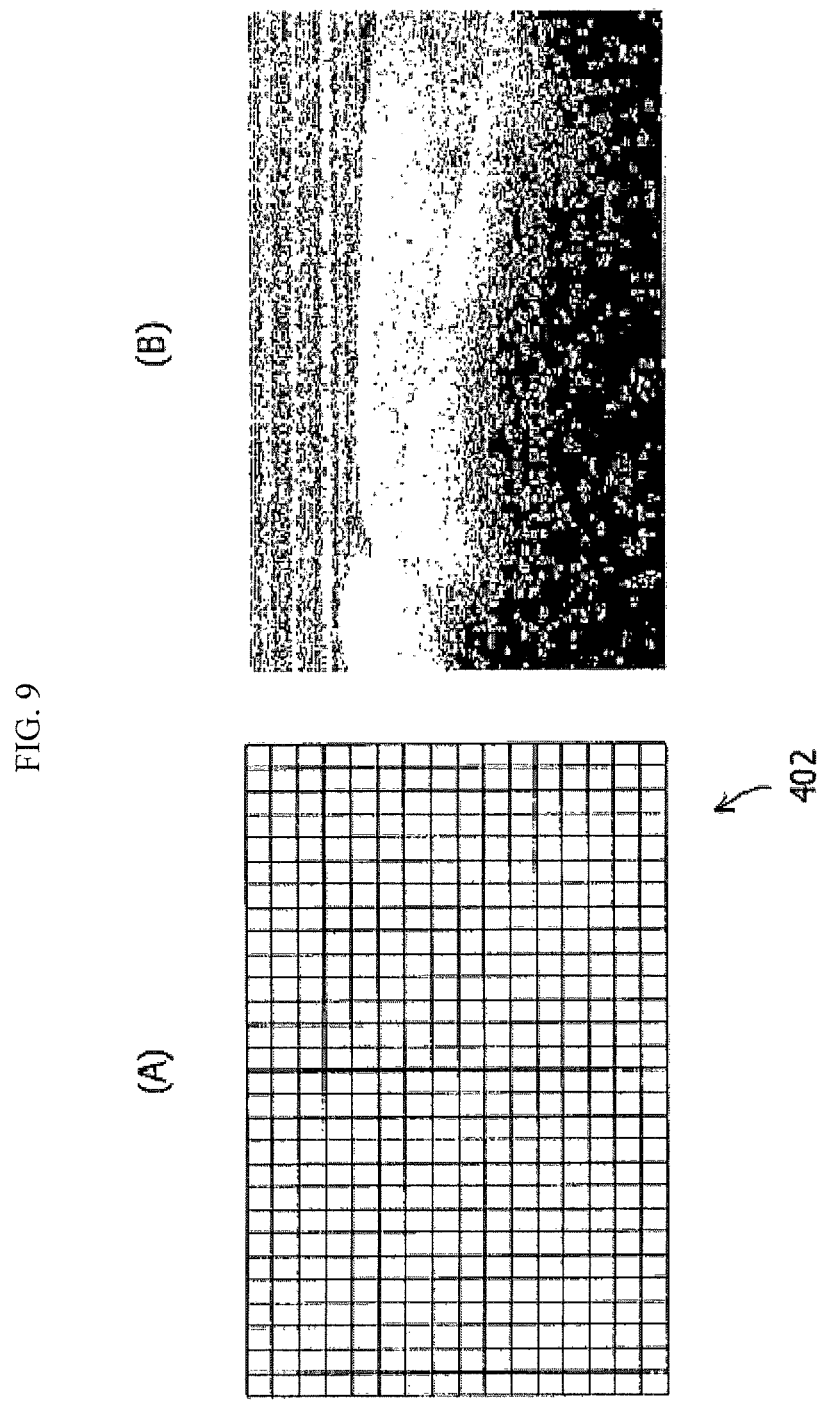
FIG. 9(A) shows a matrix created by profiling the scattering intensity values.
FIG. 9(B) shows a two-dimensional optical coherence tomographic image expressed by the difference in contrast in the form of an image in accordance with a visualizing scale.

FIG. 9 shows conversion of the matrix (A) into a two-dimensional optical coherence tomographic image (B). The two-dimensional optical coherence tomographic image is expressed in the form of monochrome density directly related to the gray level values converted from the scattering intensity values in the matrix 402. The present description has been made of the matrix 402 containing 16 rows and 28 columns by way of example, but the two-dimensional optical coherence tomographic image shown in FIG. 9(B) has been actually generated from a matrix containing 1024 pixels (rows) and 512 pixels (columns). The computing section 12 can perform the image generation operation, and the display section 14 can display the image shown in FIG. 9(B). It is noted that the two-dimensional optical coherence tomographic image shown in FIG. 9(B) represents a cross section taken along the line a-a in FIG. 3(A).

Figure 10:
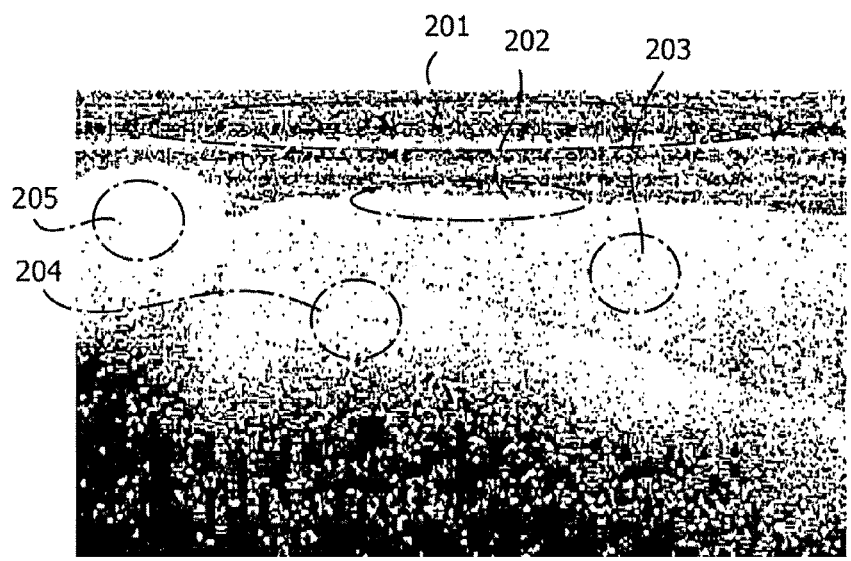
FIG. 10 shows a two-dimensional optical coherence tomographic image that allows recognition of a dental plaque region, an enamel region, and a gingiva region in an imaged region.

FIG. 10 shows the two-dimensional optical coherence tomographic image generated as described in the previous section, and the two-dimensional optical coherence tomographic image is used to extract and quantify a dental plaque region. In FIG. 10, one can recognize an air portion 201, a dental plaque region 202, an enamel region 203, a dentin region 204, and a gingiva region 205. The gray level values in these portions can, for example, be as follows: 169.4 in average (140 to 207) in the dental plaque region 202; and 95.9 in average (63 to 119) in the enamel region 203. A computer can automatically extract the dental plaque region based on these values. For example, a portion having gray level values ranging from 140 to 207 can be extracted as the dental plaque region. The extraction operation can be performed by the software that forms the measuring section 13. It is noted that the gray level values in the regions are not limited to those in the ranges described above in an exact sense but can be so set that a portion having gray level values ranging, for example, from 141 to 208 is extracted as the dental plaque region.

Therefore, the gray level values in the dental plaque region can be specified in advance and involves no decision made by a dentist or an operator for each measurement. How to specify the gray level values is, for example, as follows: A dentist examines a subject to locate a tooth on which dental plaque is clearly attached; before and after removal of the dental plaque, the dentist acquires scattering intensity values or gray level values by using an OCT apparatus; and the dentist compares the values before and after the removal of the dental plaque with each other to locate a portion where the scattering intensity values or gray level values change after the removal of the dental plaque and sets the scattering intensity values or gray level values in the portion before the dental plaque is removed to be scattering intensity values or gray level values for specifying the dental plaque region.

A description will next be made of how to acquire and display a three-dimensional image. A three-dimensional image can be generated from a plurality of sets of two-dimensional optical coherence tomographic image data by using software based on a volume rendering approach. FIG.

Figure 11:
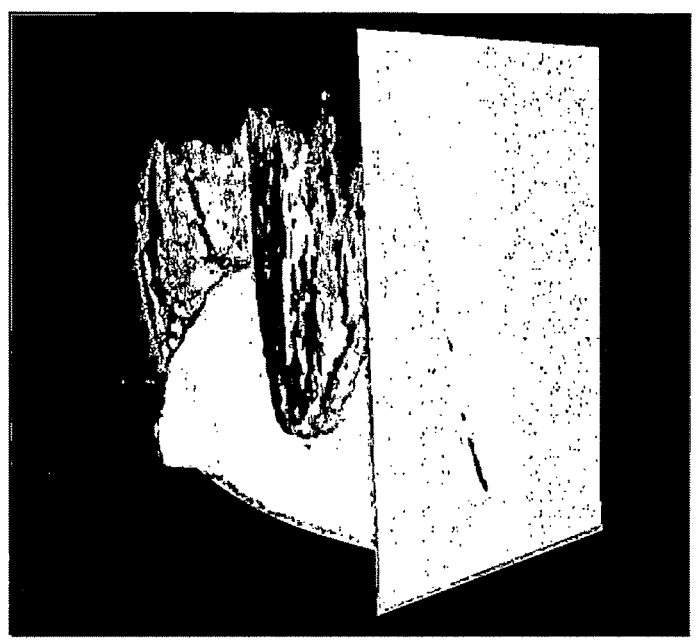
FIG. 11 shows a three-dimensional optical coherence tomographic image of a tooth generated by sequentially superimposing a plurality of two-dimensional optical coherence tomographic images of the tooth on each other.

11 shows a three-dimensional image generated from a plurality of two-dimensional optical coherence tomographic images including the image in FIG. 10. The three-dimensional image in FIG. 11 can preferably be displayed in multiple colors in the present embodiment. To generate a three-dimensional image of a front tooth, it is preferable to perform scanning in the X-axis direction in FIG. 3(B) to create two-dimensional optical coherence tomographic image data, for example, in about 200 to 300 sliced planes. An example of software that can be used to perform volume rendering may be, but not limited to, AVIZO (manufactured by Visual Science Group).

The three-dimensional image data expressed in volume by using the software allows recognition of a dental plaque region, an enamel region, a dentin region, and a gingiva region in the overall region. In a three-dimensional optical coherence tomographic image, the average of scattering intensity values in the enamel of tooth tissue on which dental plaque is attached differs from the average of scattering intensity values in the dental plaque, as in a two-dimensional optical coherence tomographic image. Based on this optical physical phenomenon, a computer is used to automatically extract a three-dimensional dental plaque region without any involvement of human decision. That is, from measurement to extraction, no person (dentist or apparatus operator) sets a value for the extraction, but voxels in a three-dimensional optical coherence tomographic image that have specific scattering intensity values can be extracted as a dental plaque region. In an embodiment, when the width of an extracted three-dimensional dental plaque region is expressed by the width of scattering intensity values, a minimum value of the width of the region can be 22.8 in average (minimum value ranges from 21.00 to 24.31) and a maximum value of the width of the region can be 39.10 in average (maximum value ranges from 37.29 to 40.89). The width of the region is not limited to these values and can be set as appropriate by a person skilled in the art in accordance with comparison based on results from known coloring methods of related art.

Figure 12:
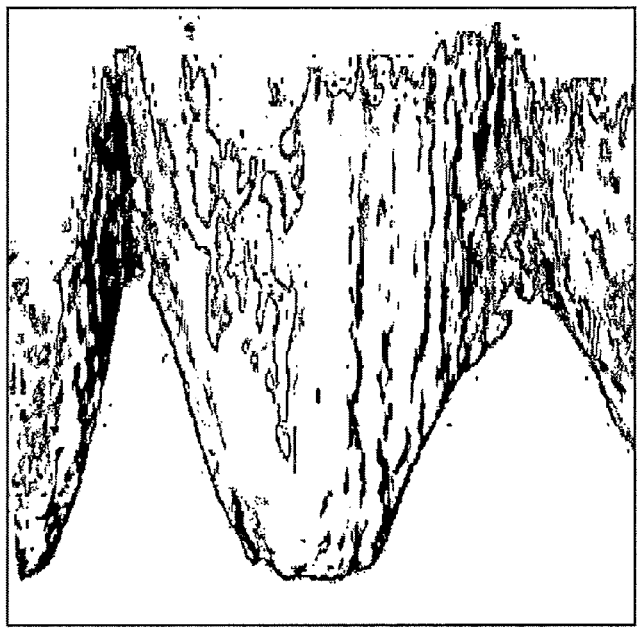
FIG. 12 shows a three-dimensionally drawn dental plaque region after the region is extracted.
Figure 13:
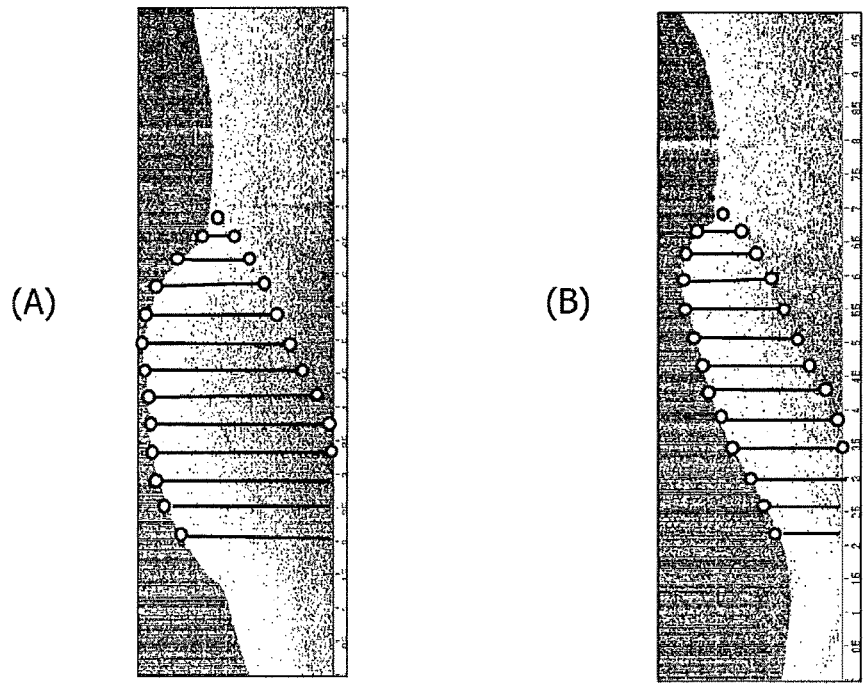
FIG. 13(A) is a two-dimensional optical coherence tomographic image of gingiva of a patient who suffers from gingivitis.
FIG. 13(B) is a two-dimensional optical coherence tomographic image of gingiva of a healthy patient.
Figure 14:
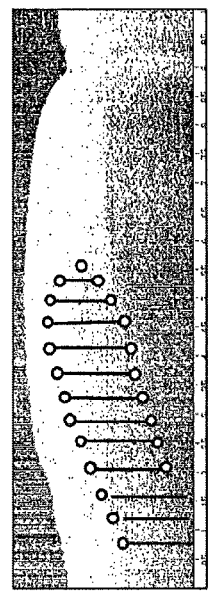
FIG. 14 is a two-dimensional optical coherence tomographic image of alveolar bone and diagrammatically shows measurement of a cross-sectional area.

The extracted dental plaque region can be displayed in the form of an image on the display section 14, for example, as shown in FIG. 12. The image shown in FIG. 12 can also preferably be displayed in multiple colors in the present embodiment.

Quantification of dental plaque will next be described. Dental plaque can be quantified in terms of the thickness of the dental plaque, the length of the dental plaque, the cross-sectional area of the dental plaque, the volume of the dental plaque, and the surface area of the dental plaque or in terms of a combination of at least one of these dimensions.
[Quantification of Thickness of Dental Plaque]

A description will be made of an example of a method for quantifying the thickness of dental plaque. To quantify the thickness of dental plaque, a dental plaque region in a two-dimensional optical coherence tomographic image in FIG. 10 is first extracted, and the number of pixels in the extracted region is counted. The number of pixels and a predetermined length (μm) per pixel in the two-dimensional optical coherence tomographic image are used to provide the thickness of the dental plaque in the two-dimensional optical coherence tomographic image. The thickness is divided by a coefficient k to provide the thickness of the dental plaque in the real space. The thickness of the dental plaque in the real space can be expressed by the following Expression (1):

The thickness of the dental plaque in the real space=a reference value (μm/pixel) used to determine the thickness of an object by using an OCT apparatus×the thickness of the extracted dental plaque region (pixels)×1/k (1)

Figure 3:
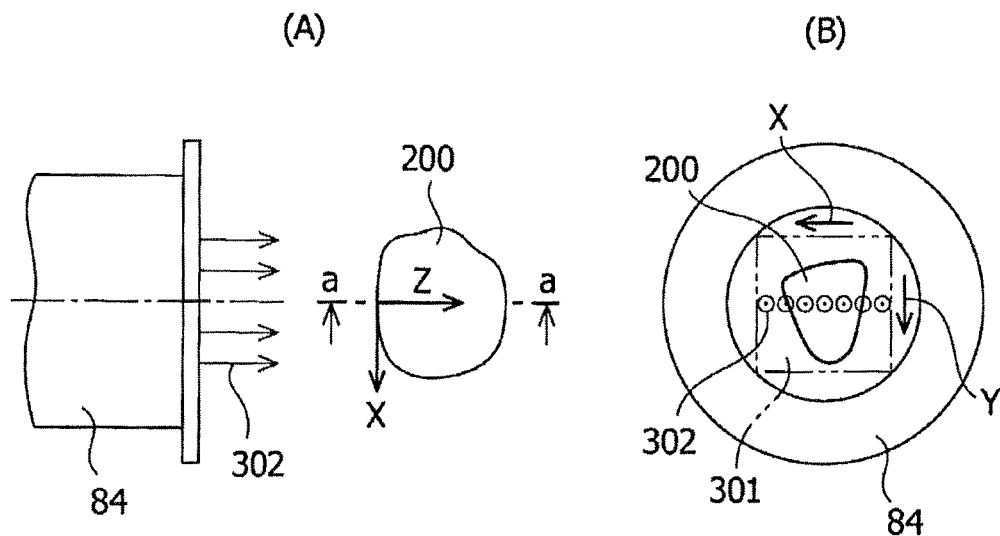
FIG. 3(A) is a schematic view of a dental plaque measuring probe front end portion and a tooth viewed from above.
FIG. 3(B) is a schematic view of the dental plaque measuring probe front end portion and the tooth viewed from a position in front of the dental plaque measuring probe front end portion.

In Expression (1), the reference value (μm/pixel) used to determine the thickness of an object by using an OCT apparatus is the length per pixel in a two-dimensional optical coherence tomographic image. In a two-dimensional optical coherence tomographic image, when the X axis, the Y axis, and the Z axis defined as shown in FIG. 3 are set, it is known that a length in the X-axis direction and a length in the Y-axis direction are displayed in full scale, but a displayed length in the Z-axis direction (depth distance) is greater than an actual dimension depending on the refractive index k of a subject. Specifically, when the refractive index of a subject is k, the length of the subject in the Z-axis direction (depth distance) displayed in a two-dimensional optical coherence tomographic image is longer than an actual dimension of the subject by a factor of k. The reference value of the thickness in Expression (1) is therefore the length per pixel of the subject displayed in the two-dimensional optical coherence tomographic image and longer than the actual dimension by a factor of k. Therefore, to acquire an actual depth distance dimension, it is necessary to multiply the reference value by the extracted number of pixels and divide the resultant depth distance displayed in the two-dimensional optical coherence tomographic image by k.

Since the above coefficient k relates to the difference in refractive index between a subject and air, the refractive index of the subject can be set at k. Typical dental plaque is primarily made of insoluble glucan and mutan and further contains oral bacteria and sugars. The refractive index k of dental plaque varies in some cases depending on the components that form the dental plaque, the content of water in the dental plaque, and other factors. The coefficient k can, for example, be set at a value ranging from about 1.30 to 1.40 and can simply be set at 1.35 but is not limited to a value within the range. The coefficient k may range from 1.1 to 2.0 or greater in some cases. The coefficient k can be determined based on the refractive index of dental plaque measured for each patient of interest, or the coefficient k can be determined by averaging measured refractive indices of dental plaque in a plurality of patients. The refractive index of dental plaque can be measured with a refractometer.

The reference value (μm/pixel) used to determine the thickness of an object by using an OCT apparatus can be determined in advance based on an object having a known thickness in the real space (length in Z-axis direction) and a known refractive index k. An object A having a thickness of 1 mm in the real space and a refractive index $k_a$ has a thickness $1 \times k_a$ (mm) when displayed in a two-dimensional optical coherence tomographic image. The reference value can therefore be calculated by dividing the thickness $1000 \times k_a$ (μm) by a pixel number count $P_{a1}$ (pixels) corresponding to the thickness of the object A actually extracted from the two-dimensional optical coherence tomographic image as follows:

The reference value (μm/pixel) used to determine the thickness of an object by using an OCT apparatus=$1000\ k_a \times 1/P_{a1}$ Once the thus determined reference value is calculated by using an OCT apparatus or software, the same value can be used afterwards.

A description will next be made of another example of the method for quantifying the thickness of dental plaque. The thickness of actual dental plaque in the subject 200 can be calculated based on the two-dimensional optical coherence tomographic image shown in FIG. 10 by the following Expression (2):

$$\text{Thickness } P \text{ of dental plaque} = Pi/k \quad (2)$$

In Expression (2), Pi represents the depth distance of the dental plaque region in the two-dimensional optical coherence tomographic image, and P represents the thickness (actual dimension) of the dental plaque. The coefficient k for deriving the actual dimension of the thickness of the dental plaque corrects the depth distance in the two-dimensional optical coherence tomographic image under the influence of the difference in refractive index between the subject and air and can be the same value used in the method described in the previous section.

In the present embodiment, the value of Pi can be acquired from the two-dimensional optical coherence tomographic image shown in FIG. 10, and the value of P can be calculated based on the value of Pi. The calculation (extraction) of the value of Pi and the calculation of the value of P can be performed by using software that forms the measuring section 13.

The thickness of dental plaque varies in some cases depending on the location where the dental plaque is measured, and the thickness of dental plaque may be the average of measurements at a plurality of measurement locations or may be a single measurement at a single location. Further, the thickness of dental plaque is not necessarily measured by the method in the present embodiment and can be measured by using other methods.

[Quantification of Length of Dental Plaque]

When the X axis, the Y axis, and the Z axis defined as shown in FIG. 3 are set, the length of dental plaque is the length along a plane defined by the X and Y axes. Since a length in the X-axis direction and a length in the Y-axis direction are displayed in full scale, the length of dental plaque in the real space can be expressed by the following Expression (3):

$$\text{The length of dental plaque in the real space} = \text{a reference value (μm/pixel) used to determine the length of an object by using an OCT apparatus} \times \text{the length (pixels) of the extracted dental plaque region} \quad (3)$$

The reference value (μm/pixel) used to determine the length of an object by using an OCT apparatus is determined as follows: That is, for example, since an object A having a length of 1 mm in the real space has the length of 1 mm also in a two-dimensional optical coherence tomographic image irrespective of the refractive index, the reference value can be calculated by dividing the length 1000 (μm) by a pixel number count $P_{a2}$ (pixels) corresponding to the length of the object A actually extracted from the two-dimensional optical coherence tomographic image as follows:

$$\text{The reference value (μm/pixel) used to determine the length of an object by using an OCT apparatus} = 1000 \times 1/P_{a2},$$

[Quantification of Cross-Sectional Area of Dental Plaque]

In measurement of the cross-sectional area of dental plaque, a dental plaque region in a two-dimensional optical coherence tomographic image is extracted. The cross-sectional area (pixels) of the extracted dental plaque region is then counted. To measure the cross-sectional area, information on the thickness in the Z-axis direction is required, as in the measurement of the thickness of dental plaque. The coefficient k used to determine the thickness of dental plaque can therefore be used along with calibration to provide the cross-sectional area in the real space.

The cross-sectional area of dental plaque in the real space can be expressed by the following Expression (4):

$$\text{The cross-sectional area of dental plaque in the real space} = \text{a reference value (μm}^2\text{/pixel) used to determine the cross-sectional area of an object by using an OCT apparatus} \times \text{the cross-sectional area (pixels) of the extracted dental plaque region} \times 1/k \quad (4)$$

The reference value (μm²/pixel) used to determine the cross-sectional area of an object by using an OCT apparatus is determined as follows: Since an object A having a cross-sectional area of 1 mm² in the real space and a refractive index $k_a$ has a cross-sectional area of $1 \times k_a$ mm² in a two-dimensional optical coherence tomographic image, the reference value can be calculated by dividing $k_a \times 10^6$ (μm²) by a pixel number count $P_{a3}$ (pixels) corresponding to the thickness of the object A actually extracted from the two-dimensional optical coherence tomographic image as follows:

$$\text{The reference value (μm}^2\text{/pixel) used to determine the cross-sectional area of an object by using an OCT apparatus} = k_a \times 10^6 \times 1/P_{a3}$$

[Quantification of Volume of Dental Plaque]

To quantify the volume of dental plaque, a dental plaque region in a three-dimensional tomographic image is first extracted. The volume (voxels) of the extracted dental plaque region is then counted. To measure the volume, information on the thickness in the Z-axis direction is also required, as in the measurement of the thickness of dental plaque. The coefficient k used to determine the thickness of dental plaque can therefore be used along with calibration to provide the volume in the real space. The volume of dental plaque in the real space can be determined by the following Expression (5):

$$\text{The volume of dental plaque in the real space} = \text{a reference value (μm}^3\text{/voxel) used to determine the volume of an object by using an OCT apparatus} \times \text{the volume (voxels) of the extracted dental plaque region} \times 1/k \quad (5)$$

The reference value (μm³/voxel) used to determine the volume of an object by using an OCT apparatus is determined as follows: Since an object A having a volume of 1 mm³ in the real space and a refractive index $k_a$ has a volume of $1 \times k_a$ mm³ in a three-dimensional optical coherence tomographic image, the reference value can be calculated by dividing $k_a \times 10^9$ (μm³) by a voxel number count $V_a$ (voxels) corresponding to the volume of the object A actually extracted from the three-dimensional optical coherence tomographic image as follows:

$$\text{The reference value (μm}^3\text{/voxel) used to determine the volume of an object by using an OCT apparatus} = k_a{'} 10^9 \times 1/V_a$$

[Quantification of Surface Area of Dental Plaque]

The surface area of dental plaque is the sum of the surface area of the dental plaque three-dimensionally in contact with air and the surface area of the dental plaque that is attached on the surface of a tooth and is a surface area of a curved dental plaque region. To quantify the surface area, a dental plaque region in a three-dimensional tomographic image is extracted, as in the measurement of the volume. The surface area (polygon areas) of the extracted dental plaque region is then counted. The surface area of the dental plaque in the real space can be determined by the following Expression (6):

The surface area of dental plaque in the real space=a reference value (μm²/polygon area) used to determine the surface area of an object by using an OCT apparatus×the surface area of the extracted dental plaque region (polygon area)    (6)

The reference value (μm²/polygon area) used to determine the surface area of an object by using an OCT apparatus is determined as follows: An object A having a surface area of 1mm² in the real space also has the surface area of 1 mm² in a three-dimensional optical coherence tomographic image. Although the depth direction distance of the extracted dental plaque region in the three-dimensional optical coherence tomographic image is longer than the depth direction distance of the dental plaque in the real space, the difference in the surface area between the real space and the optical coherence tomographic image is not large, unlike the thickness, the cross-sectional area, and the volume. The reference value can therefore be calculated by dividing $1\times10^6$ (μm²) by a polygon number count $Po_a$ (polygon areas) corresponding to the surface area of the object A actually extracted from the three-dimensional optical coherence tomographic image as follows:

The reference value (μm²/polygon area) used to determine the surface area of an object by using an OCT apparatus=$1\times10^6\times1/Po_a$ The methods described in the previous sections are methods for determining the cross-sectional area and volume of an extracted region primarily by determining the area per pixel and the volume per voxel as a reference in advance and counting the number of pixels and voxels in the extracted region in a computer. It is, however, noted that other methods for determining the area, the volume, or other parameters of an extracted region in the real space by determining the ratio of the extracted region to the entire scan range are conceivable in addition to the present embodiment and examples. The present invention is therefore not limited to the methods specifically presented in the previous sections.

The method for measuring and displaying dental plaque according to the present embodiment can further include the step of creating a database containing at least one quantified value selected from the thickness of dental plaque, the length of dental plaque, the cross-sectional area of dental plaque, the surface area of dental plaque, and the volume of dental plaque and the step of displaying the quantified value in the time course in at least one form selected from an image, a table, and a graph. In particular, the method preferably further includes the step of calculating the amount of change in the at least one quantified value of dental plaque in the time course and displaying the calculated amount of change in the time course in any form of a numerical value, a two-dimensional image, and a three-dimensional image. These steps can be carried out by using appropriate data storing and displaying system in a computer. A database containing time-course data can be useful in dental health management particularly including plaque control, periodontitis treatment, and dental caries risk reducing treatment.

The method for measuring and displaying dental plaque according to the present embodiment provides a noninvasive, safe method that allows display of an image of dental plaque and quantification of the dental plaque. The present embodiment is attained by applying an advantage of an OCT apparatus capable of acquiring information in the depth direction to measurement of dental plaque for the first time. In measurement of dental plaque and other substances that are attached on the surface of an object to a thickness of about 0.5 mm or smaller, an OCT apparatus is very useful, and the method according to the present embodiment has achieved objective quantification of dental plaque, which has not been achieved in the related art. In the image display and numerical value calculation described in the previous sections, a result can be obtained in as little as about 30 to 180seconds after infrared light irradiation. Further, since resultant data can be saved in the form of a database, the method is useful for collection of information on time-course treatment for an individual patient and collection of statistical data on dental treatment for a patient group, and the collected data can be used advantageously in the following clinical treatment. The quantification of dental plaque described in the previous sections has not been achieved before and is expected to be very useful in future dental clinical fields.

Another aspect of the present invention relates to software used in the method for measuring and displaying dental plaque described in the previous sections.

The software used in the method for measuring and displaying dental plaque along with a computer, which is a hardware resource, may form the computing section 12 and the measuring section 13, and the software extracts a dental plaque region, generates an image of the dental plaque region, and calculates the thickness, length, cross-sectional area, surface area, and/or volume of the dental plaque region, which are steps carried out by the computing section 12 and the measuring section 13 as described above. That is, the software in the present embodiment causes a computer to execute the method for measuring and displaying dental plaque and causes the computer to execute a method including the step of generating an optical coherence tomographic image based on scattering intensity values of interference light provided by the method for measuring and displaying dental plaque, the step of extracting a dental plaque region based on the optical coherence tomographic image, the step of generating an image of the dental plaque region, and the step of quantifying the dental plaque region. These steps have been substantially described in the embodiment relating to the method for measuring and displaying dental plaque, and the software along with a computer, which is a hardware resource, carries out the described steps. A more detailed description will be made below.

The step of extracting a dental plaque region may include the step of receiving an electric signal representing scattering intensity values light transmitted from the preamplifier 11 based on interference light and storing the electric signal in the form of data, the step of converting the scattering intensity values into gray level values, and the step of extracting a dental plaque region based on the gray level values. Gray level values that identify a dental plaque region can be specified in advance and are not required to be manually specified by a dentist for each measurement operation. Before the step of extracting a dental plaque region based on the gray level values, it is preferable to provide the step of smoothing the surface of the dental plaque region and the contour of the boundary between the dental plaque region and intravital tissue, such as an enamel region and a gingiva region, in a two-dimensional optical coherence tomographic image and a three-dimensional optical coherence tomographic image by performing a plurality of types of filtering on the entirety or part of the two-dimensional optical coherence tomographic image and the three-dimensional optical coherence tomographic image. It is preferable to further combine these steps with the step of morphologically identifying the intravital tissue site, such as the enamel region and the gingiva region, in each of the images based on an anatomical viewpoint. The morphological identification step is used, along with the scattering intensity values and the gray level values, to identify each site displayed in an OCT image. That is, in related art, a dentist who looks at an OCT image visually recognizes the positional relationship among the sites and the shapes thereof and identifies each of the sites in the image based on a dentist's anatomical knowledge, whereas the present invention allows the step to be carried out by using software-based morphological recognition. For example, morphological characteristics of the dental plaque region, the gingiva region, and the enamel region in the image can be recognized and identified based on anatomical facts. The regions can then be displayed in different colors in an freely selective manner. The identification step can be carried out before the step of extracting a dental plaque region. It is further preferable to provide the step of displaying the morphologically identified portions in different colors in the two-dimensional optical coherence tomographic image and/or the three-dimensional optical coherence tomographic image. Carrying out the step of extracting a dental plaque region after the morphological identification step allows reduction or elimination of wrong recognition of a dental plaque region. Further providing the additional smoothing and morphological identification steps allows extraction of a dental plaque region as accurately as a dentist's operation of manually specifying a dental plaque region.

Further, in the software according to the present embodiment, it is preferable to carry out the step of extracting a dental plaque region in relation to image capturing conditions under which an image is captured by using the dental plaque measuring probe 8. It is further preferable to carry out the step of providing at least one quantified value selected from the thickness of dental plaque, the length of dental plaque, the volume of dental plaque, the cross-sectional area of dental plaque, and the surface area of dental plaque based on the extracted dental plaque region.

The step of generating an image of the dental plaque region may include one or both of the step of generating a two-dimensional optical coherence tomographic image of the dental plaque region and the step of generating a three-dimensional optical coherence tomographic image of dental plaque region. In particular, the step of generating a three-dimensional optical coherence tomographic image of the dental plaque region can be carried out by using a volume rendering method available as an existing open source.

In the step of quantifying the dental plaque region, the thickness, length, cross-sectional area, volume, and/or surface area of the dental plaque are calculated. The calculation method may be those presented in the embodiment described in the previous sections but is not limited thereto. Once a dental plaque region is extracted, these quantitative values can be calculated based on a variety of technologies, and numerical values necessary for the calculation can be provided in the step of measuring a specific length and distance based on data displayed in the form of an image and the step of extracting the number of pixels or voxels displayed in the image.

The software according to the present embodiment causes a computer to execute the method further including the step of creating a database containing the values provided in the step of quantifying the dental plaque region and the step of displaying the quantified values in the time course in at least one form selected from an image, a table, and a graph. The creation of a database containing quantitative values and the display and/or the time-course display of an image, a table, or a graph can be performed by using known approaches.

Using the software according to the present embodiment along with a hardware resource in freely selected computer allows the extraction, generation of an image, and quantification of dental plaque and further allows the creation of a database and other operation.

[Second Embodiment : Method and Apparatus for Measuring and Displaying Gingiva and/or Alveolar Bone]

Another embodiment of the present invention relates to a method for measuring and displaying gingiva and/or alveolar bone. In the method for measuring and displaying gingiva and/or alveolar bone, the same OCT apparatus as that described in the first embodiment can be used. Infrared light is so applied to a tooth and periodontal tissue by using the OCT apparatus that scattering intensity values of interference light from the gingiva and the alveolar bone are provided, and a two-dimensional optical coherence tomographic image and/or a three-dimensional optical coherence tomographic image can then be generated.

To quantitatively evaluate swelling of gingiva and damage to alveolar bone, which lead to periodontitis, in particular, the present embodiment is characterized in that a gingiva region and an alveolar bone region are evaluated based on a two-dimensional optical coherence tomographic image and/or a three-dimensional optical coherence tomographic image. Quantitative measurement of a gingiva region and an alveolar bone region is very useful in prevention and treatment of periodontitis but has been impossible. A gingiva region and/or an alveolar bone region are distributed over a relatively wide range, unlike a dental plaque region. It is therefore difficult to capture an overall OCT image of each of the gingiva region and the alveolar bone region. It is, however, possible to capture images of the following regions and phenomena in the time-course in the same image capturing range: swelling of gingiva, absorption of alveolar bone, that is, extension of gingiva and/or alveolar bone regions, curing the swelling, that is, decrease in the gingiva region and follow-up of alveolar bone.

The method for measuring and displaying gingiva and/or alveolar bone according to the present embodiment includes the steps of dividing near infrared light output from a light source into measurement light and reference light, applying the measurement light toward a tooth and periodontal tissue in an oral cavity and scanning the tooth and the periodontal tissue with the measurement light, producing interference light from reflected light and back-scattered light from the tooth and the periodontal tissue and the reference light, generating an optical coherence tomographic image based on a scattering intensity value of the interference light, extracting a gingiva region and/or an alveolar bone region each having a specific scattering intensity value, quantifying the gingiva and/or the alveolar bone, and generating an image of the gingiva and/or the alveolar bone. The method further includes the step of obtaining the amount of change in swelling of the gingiva and/or the amount of change in the alveolar bone by carrying out the step of quantifying gingiva and/or alveolar bone in the time course.

The steps up to the step of generating an optical coherence tomographic image based on a scattering intensity value of the interference light are the same as in the first embodiment and can be carried out in the same manner as in the first embodiment to generate a two-dimensional optical coherence tomographic image or a three-dimensional optical coherence tomographic image.

[Quantification of Gingiva]

The step of extracting a gingiva region can be carried out by specifying gray level values representing the gingiva region and extracting a portion having the specific gray level values, as in the case of the other regions described in the first embodiment. The gray level values representing the gingiva region can, for example, range from 119 to 142. The gray level values within such a range can be so determined that conversion of scattering intensity values provided in OCT measurement allows the contrast across the OCT image to be most uniform in a clinical manner. It is preferable to further provide, before the step of extracting a gingiva region, the step of morphologically identifying a gingiva region in the optical coherence tomographic image based on an anatomical fact. The morphological identification step based on an anatomical fact allows the extraction of a gingiva region to be more readily and accurately performed.

In the quantification of gingiva, it is preferable to primarily quantify the volume and/or cross-sectional area of the gingiva within an image capturing range.

In the step of digitizing the volume of the gingiva, the volume in a three-dimensional optical coherence tomographic image is determined by calculating the volume per voxel in the three-dimensional optical coherence tomographic image in advance and counting the number of voxels in the gingiva region extracted from the three-dimensional optical coherence tomographic image, as in the quantification of the volume of dental plaque. The determined volume is further divided by a calibration factor k that calibrates a distance in the depth direction in the OCT measurement to digitize the volume of the gingiva. The volume of the gingiva can be expressed in a simple and plain manner as follows:

> The volume of gingiva in the real space=the reference value ($mm^3$/voxel) used to determine the volume of an object by using an OCT apparatus×the volume of the extracted gingiva region (voxels)×$1/k$ Similarly, in the step of digitizing the cross-sectional area of the gingiva, the cross-sectional area in a two-dimensional optical coherence tomographic image is determined by calculating the area per pixel in the two-dimensional optical coherence tomographic image in advance and counting the number of pixels in the gingiva region extracted from the two-dimensional optical coherence tomographic image. The determined cross-sectional area is further divided by the calibration factor k that calibrates a distance in the depth direction in the OCT measurement to digitize the cross-sectional area of the gingiva. The cross-sectional area of gingiva is expressed by the following expression. The calibration factor k in this case can be determined based on the refractive index of the gingiva, as in the case of the calibration factor k used to quantify dental plaque. A refractive index of 1.38, which is the refractive index of a living body, can be used as an approximation of the calibration factor k, and the calibration factor k can range, but not limited to, for example, from 1.3 to 1.4.

> The cross-sectional area of gingiva in the real space=the reference value ($mm^2$/pixel) used to determine the cross-sectional area of an object by using an OCT apparatus×the cross-sectional area (pixels) of the extracted gingiva region/×$1/k$ In the step of acquiring the amount of change in swelling of the gingiva, the volume and/or the cross-sectional area of the gingiva of a single patient is measured in the time course to acquire the amount of change in the volume and/or the cross-sectional area. When the gingiva is swelling, the amount of change in the swelling, in particular, can be acquired.

Even when the gingiva is not swelling, the gingiva is measured in some cases. Acquisition of the amount of change in the quantified values allows evaluation whether or not the gingiva is swelling or quantitative evaluation of the state of the gingiva and other factors thereof in the course of treatment.

[Quantification of Alveolar Bone]

A description will next be made of digitization of alveolar bone. The step of extracting an alveolar bone region can be carried out by specifying gray level values representing the alveolar bone region and extracting a portion having the specific gray level values, as in the case of the other regions described in the first embodiment and the gingiva region. The gray level values representing the alveolar bone region can, for example, range from 45 to 70. It is preferable to further provide, before the step of extracting an alveolar bone region, the step of morphologically identifying an alveolar bone region in the optical coherence tomographic image based on an anatomical fact.

The digitization of the volume and cross-sectional area of the alveolar bone can be performed as in the case of the gingiva and can be expressed by the following expressions. The calibration factor k in this case can also be determined based on the refractive index of the alveolar bone. The refractive index of 1.38, which is the refractive index of a living body, can be used as an approximation of the coefficient k, and the coefficient k can range, but not limited to, for example, from 1.3 to 1.4. In some case, the coefficient k can range from 1.1 to 2.0 or greater.

> The volume of alveolar bone in the real space=the reference value ($mm^3$/voxel) used to determine the volume of an object by using an OCT apparatus×the volume (voxels) of the extracted alveolar bone region×$1/k$ > The cross-sectional area of alveolar bone in the real space=the reference value ($mm^2$/pixel) used to determine the cross-sectional area of an object by using an OCT apparatus×the cross-sectional area (pixels) of the extracted alveolar bone region×$1/k$ In the step of acquiring the amount of change in the alveolar bone, the thus determined volume and cross-sectional area of the alveolar bone in the real space are measured in the time course, and changes in the volume and cross-sectional area are recorded. Since gingivitis is accompanied by damage to alveolar bone, a decrease in quantitative value of alveolar bone suggests development of gingivitis. Acquiring the decrease in a quantitative manner in the time course allows the state of the disease to be more readily monitored.

In the step of generating an image of the gingiva and/or the alveolar bone, in a two-dimensional optical coherence tomographic image or a three-dimensional optical coherence tomographic image, the gingiva region and/or the alveolar bone region can be distinguished from the dental plaque region and the enamel region and displayed in the form of colored regions as required.

The method and apparatus for measuring and displaying gingiva and/or alveolar bone can quantitatively grasp an intravital state that is directly related to the state of gingivitis, greatly contributing to dental treatment.

The present invention will be described in more detail with reference to Examples. The present invention is not limited to the following Examples.

EXAMPLE 1

[Measurement of Gray Level Values In Dental Plaque Region and Enamel Region (Two-dimensional Tomographic Image: 50 Slices)]

A light source that emits near infrared light, which is harmless to living bodies, was used as the light source and the dental plaque measuring probe shown in FIG. 2 was used to capture an image of a front tooth of a patient as the subject. Image software photoshop (manufactured by Adobe Systems Software Ireland Ltd) was used to measure gray level values in 150 sites in a dental plaque region and an enamel region in a two-dimensional tomographic image generated through conversion of scattering intensity values obtained from the subject into gray level values. As a result, it was ascertained that the gray level values in the enamel region and the gray level values in the dental plaque region differed from each other.

<Gray Level Values>
Dental plaque region: 169. 4 in average (maximum of 207 to minimum of 140)
Enamel region: 95.9 in average (maximum of 119 to minimum of 63)
(Significance was recognized in Welch's t test. **$P<0.01$)

<Scattering Intensity Values>
Dental plaque: 30 in average (maximum of 39 to minimum of 24)
Enamel: 13 in average (maximum of 16 to minimum of −4)

Table 1 and Table 2 show results of the gray level value measurement in the dental plaque region and the enamel region.

TABLE 1

| Case | Slice | Plaque | enamel |
|---|---|---|---|
| 1 | 1 | 143 | 72 |
|  |  | 140 | 92 |
|  |  | 158 | 65 |
|  | 2 | 166 | 94 |
|  |  | 177 | 88 |
|  |  | 193 | 63 |
|  | 3 | 173 | 104 |
|  |  | 165 | 98 |
|  |  | 153 | 74 |
|  | 4 | 178 | 89 |
|  |  | 169 | 93 |
|  |  | 189 | 87 |
|  | 5 | 199 | 84 |
|  |  | 175 | 98 |
|  |  | 173 | 109 |
| 2 | 1 | 158 | 104 |
|  |  | 173 | 96 |
|  |  | 182 | 115 |
|  | 2 | 185 | 86 |
|  |  | 191 | 116 |
|  |  | 168 | 101 |
|  | 3 | 190 | 95 |
|  |  | 155 | 98 |
|  |  | 163 | 103 |
|  | 4 | 186 | 101 |
|  |  | 198 | 85 |
|  |  | 151 | 85 |
|  | 5 | 168 | 104 |
|  |  | 189 | 95 |
|  |  | 166 | 67 |
| 3 | 1 | 197 | 116 |
|  |  | 207 | 85 |
|  |  | 161 | 107 |
|  | 2 | 166 | 109 |
|  |  | 140 | 118 |
|  |  | 146 | 79 |
|  | 3 | 156 | 97 |
|  |  | 147 | 95 |
|  |  | 140 | 103 |
|  | 4 | 148 | 113 |
|  |  | 142 | 114 |
|  |  | 146 | 99 |
|  | 5 | 153 | 103 |
|  |  | 170 | 114 |
|  |  | 167 | 76 |
| 4 | 1 | 186 | 97 |
|  |  | 160 | 117 |
|  |  | 174 | 104 |
|  | 2 | 199 | 114 |
|  |  | 163 | 90 |
|  |  | 173 | 117 |
|  | 3 | 169 | 114 |
|  |  | 183 | 102 |
|  |  | 174 | 98 |
|  | 4 | 188 | 104 |
|  |  | 163 | 96 |
|  |  | 169 | 97 |
|  | 5 | 160 | 85 |
|  |  | 195 | 110 |
|  |  | 167 | 81 |
| 5 | 1 | 173 | 108 |
|  |  | 188 | 94 |
|  |  | 164 | 111 |
|  | 2 | 148 | 90 |
|  |  | 160 | 102 |
|  |  | 162 | 87 |
|  | 3 | 176 | 91 |
|  |  | 157 | 87 |
|  |  | 149 | 118 |
|  | 4 | 173 | 95 |
|  |  | 162 | 102 |
|  |  | 149 | 78 |
|  | 5 | 171 | 83 |
|  |  | 145 | 107 |
|  |  | 149 | 87 |
| 6 | 1 | 171 | 95 |
|  |  | 178 | 96 |
|  |  | 163 | 82 |
|  | 2 | 165 | 93 |
|  |  | 186 | 116 |
|  |  | 163 | 95 |
|  | 3 | 140 | 106 |
|  |  | 164 | 93 |
|  |  | 181 | 112 |
|  | 4 | 162 | 103 |
|  |  | 168 | 73 |
|  |  | 142 | 63 |
|  | 5 | 164 | 98 |
|  |  | 175 | 109 |
|  |  | 149 | 114 |

TABLE 2

| Case | Slice | Plaque | enamel |
|---|---|---|---|
| 7 | 1 | 185 | 84 |
|  |  | 193 | 107 |
|  |  | 159 | 89 |
|  | 2 | 167 | 119 |
|  |  | 181 | 102 |
|  |  | 170 | 110 |
|  | 3 | 168 | 114 |
|  |  | 199 | 84 |
|  |  | 188 | 96 |
|  | 4 | 185 | 108 |
|  |  | 204 | 119 |
|  |  | 177 | 96 |
|  | 5 | 192 | 107 |

TABLE 2-continued

| Case | Slice | Plaque | enamel |
|---|---|---|---|
|  |  | 184 | 94 |
|  |  | 165 | 114 |
| 8 | 1 | 205 | 98 |
|  |  | 184 | 111 |
|  |  | 182 | 74 |
|  | 2 | 189 | 85 |
|  |  | 172 | 98 |
|  |  | 152 | 107 |
|  | 3 | 175 | 93 |
|  |  | 198 | 111 |
|  |  | 171 | 104 |
|  | 4 | 183 | 110 |
|  |  | 155 | 118 |
|  |  | 200 | 92 |
|  | 5 | 179 | 96 |
|  |  | 169 | 105 |
|  |  | 190 | 103 |
| 9 | 1 | 183 | 86 |
|  |  | 168 | 91 |
|  |  | 190 | 76 |
|  | 2 | 152 | 73 |
|  |  | 195 | 101 |
|  |  | 163 | 83 |
|  | 3 | 153 | 94 |
|  |  | 174 | 108 |
|  |  | 184 | 98 |
|  | 4 | 174 | 84 |
|  |  | 172 | 104 |
|  |  | 182 | 96 |
|  | 5 | 143 | 92 |
|  |  | 152 | 95 |
|  |  | 141 | 91 |
| 10 | 1 | 174 | 92 |
|  |  | 180 | 81 |
|  |  | 168 | 96 |
|  | 2 | 148 | 91 |
|  |  | 155 | 79 |
|  |  | 166 | 83 |
|  | 3 | 148 | 109 |
|  |  | 164 | 83 |
|  |  | 144 | 69 |
|  | 4 | 151 | 75 |
|  |  | 167 | 87 |
|  |  | 155 | 94 |
|  | 5 | 162 | 72 |
|  |  | 152 | 86 |
|  |  | 149 | 63 |
| Average gray level value |  | 169.40 | 95.89 |

Table 3 shows results of the gray level value measurement in a gingiva region.

TABLE 3

| Case | Slice | Gray level value |
|---|---|---|
| 1 | 1 | 130 |
|  |  | 125 |
|  |  | 126 |
|  | 2 | 131 |
|  |  | 131 |
|  |  | 120 |
|  | 3 | 119 |
|  |  | 132 |
|  |  | 135 |
|  | 4 | 125 |
|  |  | 128 |
|  |  | 131 |
|  | 5 | 120 |
|  |  | 119 |
|  |  | 140 |
| 2 | 1 | 139 |
|  |  | 129 |
|  |  | 126 |
|  | 2 | 135 |
|  |  | 124 |
|  |  | 130 |
|  | 3 | 128 |
|  |  | 135 |
|  |  | 121 |
|  | 4 | 119 |
|  |  | 132 |
|  |  | 141 |
|  | 5 | 135 |
|  |  | 138 |
|  |  | 136 |
| 3 | 1 | 141 |
|  |  | 137 |
|  |  | 129 |
|  | 2 | 134 |
|  |  | 124 |
|  |  | 141 |
|  | 3 | 134 |
|  |  | 135 |
|  |  | 140 |
|  | 4 | 129 |
|  |  | 131 |
|  |  | 135 |
|  | 5 | 136 |
|  |  | 129 |
|  |  | 130 |
| 4 | 1 | 134 |
|  |  | 135 |
|  |  | 131 |
|  | 2 | 129 |
|  |  | 124 |
|  |  | 125 |
|  | 3 | 134 |
|  |  | 140 |
|  |  | 138 |
|  | 4 | 130 |
|  |  | 138 |
|  |  | 140 |
|  | 5 | 136 |
|  |  | 138 |
|  |  | 128 |
| 5 | 1 | 125 |
|  |  | 135 |
|  |  | 132 |
|  | 2 | 134 |
|  |  | 135 |
|  |  | 130 |
|  | 3 | 129 |
|  |  | 128 |
|  |  | 131 |
|  | 4 | 135 |
|  |  | 128 |
|  |  | 140 |
|  | 5 | 131 |
|  |  | 138 |
|  |  | 139 |
| 6 | 1 | 138 |
|  |  | 128 |
|  |  | 131 |
|  | 2 | 127 |
|  |  | 126 |
|  |  | 125 |
|  | 3 | 134 |
|  |  | 133 |
|  |  | 141 |
|  | 4 | 136 |
|  |  | 133 |
|  |  | 137 |
|  | 5 | 129 |
|  |  | 141 |
|  |  | 135 |
| 7 | 1 | 134 |

TABLE 3-continued

| Case | Slice | Gray level value |
|---|---|---|
| | | 129 |
| | | 133 |
| | 2 | 135 |
| | | 138 |
| | | 131 |
| | 3 | 138 |
| | | 137 |
| | | 134 |
| | 4 | 142 |
| | | 137 |
| | | 138 |
| | 5 | 132 |
| | | 135 |
| | | 136 |
| 8 | 1 | 134 |
| | | 131 |
| | | 130 |
| | 2 | 134 |
| | | 140 |
| | | 138 |
| | 3 | 132 |
| | | 128 |
| | | 134 |
| | 4 | 135 |
| | | 133 |
| | | 135 |
| | 5 | 132 |
| | | 139 |
| | | 140 |
| 9 | 1 | 137 |
| | | 132 |
| | | 134 |
| | 2 | 136 |
| | | 135 |
| | | 132 |
| | 3 | 133 |
| | | 134 |
| | | 128 |
| | 4 | 136 |
| | | 142 |
| | | 138 |
| | 5 | 134 |
| | | 136 |
| | | 129 |
| 10 | 1 | 135 |
| | | 139 |
| | | 134 |
| | 2 | 133 |
| | | 134 |
| | | 141 |
| | 3 | 142 |
| | | 135 |
| | | 132 |
| | 4 | 138 |
| | | 127 |
| | | 138 |
| | 5 | 137 |
| | | 132 |
| | | 139 |

<Gray Level Values>

Gingiva region: 133.1 in average (maximum of 142 to minimum of 119)

Table 4 shows results of the gray level value measurement in an alveolar bone region.

TABLE 4

| Case | Slice | Gray level value |
|---|---|---|
| 1 | 1 | 67 |
| | | 69 |
| | | 64 |
| | 2 | 65 |
| | | 70 |
| | | 68 |
| | 3 | 57 |
| | | 68 |
| | | 54 |
| | 4 | 59 |
| | | 56 |
| | | 64 |
| | 5 | 48 |
| | | 68 |
| | | 58 |
| 2 | 1 | 57 |
| | | 68 |
| | | 54 |
| | 2 | 51 |
| | | 48 |
| | | 59 |
| | 3 | 57 |
| | | 51 |
| | | 64 |
| | 4 | 61 |
| | | 58 |
| | | 54 |
| | 5 | 49 |
| | | 57 |
| | | 58 |
| 3 | 1 | 55 |
| | | 64 |
| | | 59 |
| | 2 | 62 |
| | | 58 |
| | | 47 |
| | 3 | 58 |
| | | 55 |
| | | 57 |
| | 4 | 48 |
| | | 62 |
| | | 65 |
| | 5 | 54 |
| | | 57 |
| | | 49 |
| 4 | 1 | 65 |
| | | 61 |
| | | 58 |
| | 2 | 57 |
| | | 54 |
| | | 55 |
| | 3 | 64 |
| | | 59 |
| | | 48 |
| | 4 | 59 |
| | | 55 |
| | | 51 |
| | 5 | 52 |
| | | 57 |
| | | 59 |
| 5 | 1 | 56 |
| | | 54 |
| | | 66 |
| | 2 | 61 |
| | | 58 |
| | | 54 |
| | 3 | 55 |
| | | 58 |
| | | 59 |
| | 4 | 64 |
| | | 61 |
| | | 58 |
| | 5 | 57 |
| | | 55 |
| | | 52 |
| 6 | 1 | 49 |

TABLE 4-continued

| Case | Slice | Gray level value |
|---|---|---|
|  |  | 58 |
|  |  | 56 |
|  | 2 | 64 |
|  |  | 56 |
|  |  | 58 |
|  | 3 | 55 |
|  |  | 51 |
|  |  | 56 |
|  | 4 | 52 |
|  |  | 61 |
|  |  | 49 |
|  | 5 | 61 |
|  |  | 57 |
|  |  | 49 |
| 7 | 1 | 55 |
|  |  | 58 |
|  |  | 59 |
|  | 2 | 57 |
|  |  | 61 |
|  |  | 47 |
|  | 3 | 54 |
|  |  | 58 |
|  |  | 54 |
|  | 4 | 56 |
|  |  | 56 |
|  |  | 57 |
|  | 5 | 54 |
|  |  | 48 |
|  |  | 56 |
| 8 | 1 | 58 |
|  |  | 54 |
|  |  | 57 |
|  | 2 | 48 |
|  |  | 65 |
|  |  | 48 |
|  | 3 | 61 |
|  |  | 67 |
|  |  | 48 |
|  | 4 | 56 |
|  |  | 58 |
|  |  | 55 |
|  | 5 | 54 |
|  |  | 54 |
|  |  | 51 |
| 9 | 1 | 58 |
|  |  | 59 |
|  |  | 56 |
|  | 2 | 61 |
|  |  | 64 |
|  |  | 48 |
|  | 3 | 55 |
|  |  | 57 |
|  |  | 57 |
|  | 4 | 54 |
|  |  | 51 |
|  |  | 48 |
|  | 5 | 45 |
|  |  | 56 |
|  |  | 52 |
| 10 | 1 | 53 |
|  |  | 51 |
|  |  | 58 |
|  | 2 | 54 |
|  |  | 55 |
|  |  | 49 |
|  | 3 | 56 |
|  |  | 57 |
|  |  | 58 |
|  | 4 | 61 |
|  |  | 58 |
|  |  | 54 |
|  | 5 | 58 |
|  |  | 55 |
|  |  | 59 |

<Gray Level Values>
Alveolar bone region: 56.8 in average (maximum of 45 to minimum of 70)

EXAMPLE 2

[Calculation of Thickness, Length, and Cross-Sectional Area of Dental Plaque (Two-Dimensional Tomographic Image: 10 Slices)]

<Calculation Method 1>

In the present example, reference used to determine the thickness, length, and cross-sectional area of an object (dental plaque) by using an OCT apparatus were determined in advance. A post-polymerization polymer material in a box-like shape having dimensions of 5×5×1 mm in the real space was imaged by using the OCT apparatus, and the thickness (pixels), the length (pixels), and the cross-sectional area (pixels) in a two-dimensional optical coherence tomographic image were obtained. The two-dimensional optical coherence tomographic image was analyzed by using Photoshop cs5 (adobe(™)).

<Results of Calculation Method 1>

TABLE 5

|  |  | OCT space | |
|---|---|---|---|
|  | Real space | Value calibrated based on refractive index | Count in region of interest in two-dimensional optical coherence tomographic image |
| Thickness | 1 mm | 1.65 mm | 86 pixel (on two-dimensional optical coherence tomographic image) |
| Length | 5 mm | 5 mm | 381 pixel (on two-dimensional optical coherence tomographic image) |
| Cross-sectional area | 5 mm$^2$ | 8.25 mm$^2$ | 32766 pixel (on two-dimensional optical coherence tomographic image) |

According to the result described above, the reference used to determine the thickness of an object by using an OCT apparatus was obtained as follows:

1.65 mm/86 pixels=0.0192 . . . mm/pixel (19.2 μm/pixel)

The reference used to determine the length of an object by using an OCT apparatus was obtained as follows:

5 mm/381 pixels=0.0131 . . . mm/pixel (13.1 μm/pixel)

The reference used to determine the cross-sectional area of an object by using an OCT apparatus was obtained as follows:

8.25 mm$^2$/32766 pixels=0.000251785 . . . mm$^2$/pixel (about 250 μm$^2$/pixel)

In the present example, the calibration factor that calibrates a distance in the depth direction in OCT measurement based on the refractive index of dental plaque was set at 1.35.

<Calculation Method 2>

A dental plaque region in a two-dimensional tomographic image was extracted based on the fact that the gray level values in the dental plaque region and the gray level values in the enamel region differed from each other as shown in Example 1. The thickness, length, and the cross-sectional area (pixels) in the extracted dental plaque region were then counted. The two-dimensional optical coherence tomographic image was analyzed by using Photoshop cs5 (manufactured by adobe™ Systems Software Ireland Ltd).

The thickness was measured by using the following expression, and k was set at 1.35:

The thickness of dental plaque in the real space=(the reference value used to determine the thickness of an object by using an OCT apparatus: 19.2 μm/pixel)×the thickness (pixels)×1/k The length was measured by using the following expression:

The length of dental plaque in the real space=(the reference value used to determine the length of an object by using an OCT apparatus: 13.1 μm/pixel)×the length (pixels)

The cross-sectional area was measured by using the following expression:

The cross-sectional area of dental plaque in the real space=(the reference value used to determine the cross-sectional area of an object by using an OCT apparatus: 250 μm$^2$/pixel)×the cross-sectional area (pixels)×1/k <Results of Calculation Method 2>

Table 6 shows the resultant thickness, length, and cross-sectional area of dental plaque. Cases 1 to 10 correspond to the cases 1 to 10 in Example 1. The results in the upper portion of the table show values (pixels) in the OCT space, and the results in the lower portion of the table show values (meters) in the real space.

TABLE 6

| | Case | Thickness pixel | Length pixel | Cross-sectional area pixel |
|---|---|---|---|---|
| OCT space | 2D-1 | 23 | 461 | 3938 |
| | 2D-2 | 82 | 208 | 2279 |
| | 2D-3 | 27 | 92 | 891 |
| | 2D-4 | 71 | 94 | 1187 |
| | 2D-5 | 29 | 239 | 1899 |
| | 2D-6 | 55 | 558 | 6304 |
| | 2D-7 | 17 | 129 | 1019 |
| | 2D-8 | 26 | 94 | 875 |
| | 2D-9 | 70 | 99 | 1419 |
| | 2D-10 | 73 | 121 | 1939 |

| | | Thickness | | Length | Cross-sectional area |
|---|---|---|---|---|---|
| | Case | mm | μm | mm | mm$^2$ |
| Real space | 2D-1 | 0.327 | 327 | 6.0 | 0.73 |
| | 2D-2 | 1.165 | 1165 | 2.7 | 0.42 |
| | 2D-3 | 0.384 | 384 | 1.2 | 0.17 |
| | 2D-4 | 1.009 | 1009 | 1.2 | 0.22 |
| | 2D-5 | 0.412 | 412 | 3.1 | 0.35 |
| | 2D-6 | 0.782 | 782 | 7.3 | 1.17 |
| | 2D-7 | 0.242 | 242 | 1.7 | 0.19 |
| | 2D-8 | 0.370 | 370 | 1.2 | 0.16 |
| | 2D-9 | 0.995 | 995 | 1.3 | 0.26 |
| | 2D-10 | 1.037 | 1037 | 1.6 | 0.36 |

EXAMPLE 3

[Extraction of Dental Plaque Region with Respect to Dental Plaque Coloring Method]

First, two-dimensional data was converted into three-dimensional data. A computer was used to perform automatic computational processing on the interference light to provide float data, which was introduced into software AVIZO (manufactured by Visual Sciences Group), which performs volume rendering to generate a three-dimensional image. One freely chosen voxel in a dental plaque region was then selected in the software AVIZO. The dental plaque region was extracted in AVIZO by using a method for adjusting the width of the region in such a way that the selected region coincides with the region in a photograph of colored dental plaque (adjusting minimum and maximum of scattering intensity values).

As a result, the minimum of the width of the region was 22.8 on average (minimum ranges from 21.00 to 24.31), and the maximum of the width of the region was 39.10 on average (maximum ranges from 37.29 to 40.89). Table 3 shows results of the extraction of the dental plaque region with respect to the dental plaque coloring method. Cases 1 to 10 correspond to the cases 1 to 10 in Examples 1 and 2.

TABLE 7

| Case | Minimum | Maximum |
|---|---|---|
| 1 | 22.00 | 38.00 |
| 2 | 24.20 | 39.52 |
| 3 | 24.31 | 39.19 |
| 4 | 21.48 | 37.29 |
| 5 | 21.00 | 40.02 |
| 6 | 23.38 | 40.38 |
| 7 | 24.06 | 38.66 |
| 8 | 22.01 | 38.00 |
| 9 | 22.27 | 39.01 |
| 10 | 23.78 | 40.89 |
| Average | 22.85 | 39.10 |

EXAMPLE 4

[Calculation of Volume of Extracted Dental Plaque]
<Calculation Method 1>

In the present example, reference used to determine the volume and surface area of an object (dental plaque) by using an OCT apparatus were determined in advance. A post-polymerization polymer material in a box-like shape having dimensions of 5×5×1 mm in the real space was imaged by using the OCT apparatus, and the volume (voxels) and the surface area (areas) in a two-dimensional optical coherence tomographic image were obtained. The three-dimensional optical coherence tomographic image was analyzed by using AVIZO (manufactured by Visual Sciences Group).

<Results of Calculation Method 1>

TABLE 8

| | | | OCT space | |
|---|---|---|---|---|
| | Real space | Value calibrated based on refractive index | Count in region of interest in three-dimensional optical coherence tomographic image | |
| Volume | 25 mm$^3$ | 41.25 mm$^3$ | 90745512 | voxel (on three-dimensional optical coherence tomographic image) |
| Surface area | 70 mm$^2$ | 83 mm$^2$ | 2325298 | polygon area (on three-dimensional optical coherence tomographic image) |

According to the results described above, the reference value was obtained as follows:

The reference value used to determine the volume of an object by using an OCT apparatus:

41.25 mm³/90745512 voxels=0.0000004545 . . . mm³/voxel (about 454.5 μm³/voxel)

The reference value used to determine the surface area of an object by using an OCT apparatus:

83 mm²/2325298 polygon areas=0.00003569 . . . mm²/polygon area (about 35.7 μm²/polygon area)

The calibration factor that calibrates a distance in the depth direction in OCT measurement based on the refractive index of dental plaque: k=1.35

<Calculation Method 2>

A dental plaque region in a three-dimensional tomographic image was extracted based on the fact that the gray level values in the dental plaque region and the gray level values in the enamel region differed from each other as shown in Example 1. The volume (voxels) and the surface area (areas) in the extracted dental plaque region were then counted. The three-dimensional optical coherence tomographic image was analyzed by using AVIZO (manufactured by Visual Sciences Group).

The volume was measured by using the following expression:

The volume of dental plaque in the real space=(the reference used to determine the volume of an object by using an OCT apparatus)×the volume (voxels)×1/k (k=1.35)

The surface area was measured by using the following expression:

The surface area of dental plaque in the real space= (the reference used to determine the surface area of an object by using an OCT apparatus)× the surface area (polygon areas)

<Results of Calculation Method 2>

TABLE 9

| Case | Surface area On three-dimensional optical coherence tomographic image (area: polygon) | Real space (mm²) | Volume On three-dimensional optical coherence tomographic image (volume: voxel) | Real space (mm³) |
|---|---|---|---|---|
| 1 | 661041 | 23.6 | 2305619 | 0.78 |
| 2 | 494417 | 17.6 | 2054341 | 0.69 |
| 3 | 420864 | 15.0 | 1704007 | 0.57 |
| 4 | 224719 | 8.0 | 386498 | 0.13 |
| 5 | 88881 | 3.2 | 330249 | 0.11 |
| 6 | 1000071 | 35.7 | 3573267 | 1.20 |
| 7 | 307162 | 11.0 | 1318459 | 0.44 |
| 8 | 982007 | 35.1 | 5021140 | 1.69 |
| 9 | 820506 | 29.3 | 3471171 | 1.17 |
| 10 | 737557 | 26.3 | 1994682 | 0.67 |
| Average | 573722.5 | 20.5 | 2215943.3 | 0.75 |

EXAMPLE 5

[Quantification of Gingiva and/or Alveolar Bone]

(1) Quantification of Gingiva

A gingiva region was extracted from a two-dimensional optical coherence tomographic image, and the cross-sectional area (pixels) of the extracted gingiva region was determined on the OCT image. Since the gingiva region in the OCT image is extended in the depth direction as compared with the gingiva region in the real space, the gingiva region was calibrated based on the refractive index to determine the cross-sectional area of the gingiva in the real space. The coefficient k was set at 1.38. Although the refractive index of gingiva varies depending on the degrees of inflammation and characters of the gingiva in an exact sense, the calibration factor k was believed to be nearly equal to the refractive index of a living body (ne≈1.38), and the calibration factor k was set at 1.38 in the present example.

The cross-sectional area of gingiva in the real space=(the reference used to determine the cross-sectional area of an object by using an OCT apparatus)×the cross-sectional area (pixels)/×1/1.38

Table 10 below shows the cross-sectional area of the gingiva determined by using the OCT apparatus.

TABLE 10

| | Cross-sectional area (on OCT image) pixel | Cross-sectional area (on real space) mm² |
|---|---|---|
| Antiphlogistic gingiva | 36320 | 6.6 |
| Inflammatory gingiva | 59892 | 10.9 |

(2) Quantification of Alveolar Bone

An alveolar bone region was extracted from a two-dimensional optical coherence tomographic image, and the cross-sectional area (pixels) of the extracted alveolar bone region was determined on the OCT image. Since the alveolar bone region in the OCT image is extended in the depth direction as compared with the alveolar bone region in the real space, the alveolar bone region was calibrated based on the refractive index to determine the cross-sectional area of the alveolar bone in the real space. The coefficient k was set at 1.38. Although the refractive index of alveolar bone varies depending on the amount of blood flow in the alveolar bone and other factors in an exact sense, the calibration factor k was believed to be nearly equal to the refractive index of a living body (ne≈1.38), and the calibration factor k was set at 1.38 in the present example.

The cross-sectional area of alveolar bone in the real space=(the reference used to determine the cross-sectional area of an object by using an OCT apparatus)×the cross-sectional area (pixels)/×1/1.38

Table 11 below shows the cross-sectional area of the alveolar bone determined by using the OCT apparatus.

TABLE 11

| | Cross-sectional area (on OCT image) pixel | Cross-sectional area (on real space) mm² |
|---|---|---|
| Only alveolar bone | 37533 | 6.8 |

EXAMPLE 6

[Comparison with Coloring Method]

Figure 15:
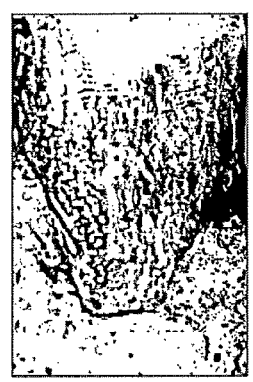
FIG. 15(A) is a photograph of oral attachment of dental plaque colored by using a coloring method of related art.
FIG. 15(B) is an image of a dental plaque region captured by using an imaging method according to the present embodiment and quantitatively measured and displayed.
Figure 15:
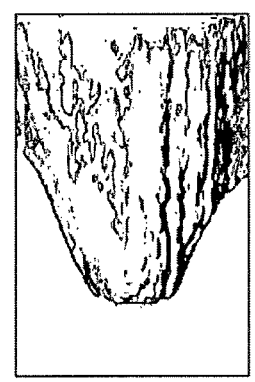

An image of dental plaque colored by using a coloring method of related art was compared with an image of dental plaque extracted, imaged, and quantitatively displayed by using the method according to the present invention. According to Plaque Control Record developed by O'Leary, 0.5 ml of DENT Plaque Tester Liquid (product name)

manufactured by Lion Corporation (manufacturer) was used as a coloring liquid to color a front tooth or a subject. FIG. 15(A) shows a photograph of the colored dental plaque.

On the other hand, a three-dimensional image was generated by using the apparatus and method according to the present invention. The scan range and the dental plaque extraction region were set under the same conditions as those in Examples 3 and 4. FIG. 15(B) shows an image of the dental plaque generated by capturing an image of an extracted dental plaque region extracted, imaged, and quantitatively displayed. FIGS. 15(A) and 15(B) indicate that the present invention allows dental plaque measurement capable of providing results sufficiently comparable with results provided by a coloring method, which is a gold standard method in the medical treatment in Japan. It is noted that FIGS. 15(A) and 15(B) are color images.

EXAMPLE 7

[Attachment of Dental Plaque under Gingival Cuff]

Figure 16:
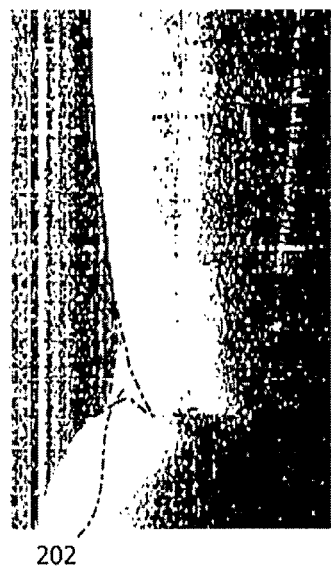
FIG. 16(A) is an optical coherence tomographic image that has captured the attachment of dental plaque under a gingival cuff.
FIG. 16(B) is a diagrammatic view of the dental plaque attachment.
Figure 16:
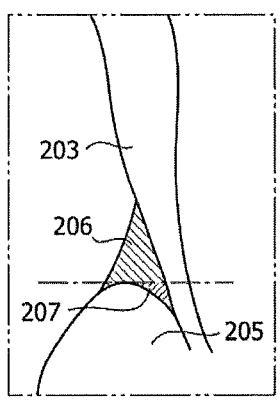

The method and apparatus according to the present invention were used to capture a two-dimensional tomographic image of another subject. The dental plaque extraction region was set in the same manner as in Example 2. The scan range was so set that gingival cuff and a portion about 3 mm under the gingival cuff fall within the image capturing range. FIG. 16(A) shows an optical coherence tomographic image containing attachment of dental plaque under the gingival cuff. FIG. 16(B) is a diagrammatic view of the dental plaque attachment based on the image in FIG. 16(A). In FIG. 16(A), one can clearly recognize dental plaque 202. FIG. 16(B) diagrammatically shows dental plaque between an enamel 203 and gingiva 205, specifically, dental plaque 206 over the gingival cuff and dental plaque 207 under the gingival cuff. It was indicated that the present invention allows objective, quantitatively measurement of dental plaque attached under a gingival cuff, which has never been successfully measured.

INDUSTRIAL APPLICABILITY

Dental caries and periodontitis, which are two major dental diseases, result primarily from dental plaque, and society ages, dental plaque is believed to be not only a problem in dentistry, but also a cause of aspiration pneumonia, infectious endocarditis, and other systemic diseases. The method according to the present invention can generate an image of and digitize attachment of dental plaque, which has not been an objectively or quantitatively evaluated method, and provides an advantageous effect of encouraging more reliable dental practice.

REFERENCE SIGNS LIST

100 Apparatus for measuring and displaying dental plaque
1 Near infrared light source
3 Splitter
4 Light rectifier
5 Light modifier
6 Polarization and attenuation plate
8 Dental plaque measuring probe
9 Reference mirror
10 Light receiving element
11 Preamplifier
12 Computing section
13 Measuring section
14 Display section
15 Occlusal block for fixing image capturing position
81 Non-movable optical path control mirror
82 Movable optical path control mirror
83 Objective lens
84 Dental plaque measuring probe front portion
86 Image capturing position adjustment stage
87a Image capturing position adjustment X-axis controller
87b Image capturing position adjustment Y-axis controller
87c Image capturing position adjustment Z-axis controller
88a Image capturing position adjustment α-axis controller
88b Image capturing position adjustment β-axis controller
88c Image capturing position adjustment γ-axis controller
89 Image capturing position adjustment gonio-axis controller
200 Subject (tooth)
201 Air portion
202 Dental plaque region
203 Enamel region
204 Dentin region
205 Gingiva region
206 Dental plaque over gingival cuff
207 Dental plaque under gingival cuff
301 Measurable field of view
302 Diagrammatic path of observation light
303 Tooth axis
304 Axis parallel to orientation of measurement light
α Measurement angle (inappropriate)
R Measurement angle within appropriate range
305 Line parallel to tooth surface
β Measurement angle within inappropriate range
306 Axis parallel to orientation of measurement light
401 Matrix data (matrix) corresponding to single point and having scattering intensities arranged in single column
402 Matrix data (matrix) corresponding to single line and produced by sequentially repeating the same step for following waveforms
F Optical fiber
L Collimator lens
800 Dental plaque measuring fiber-type probe
801 Dental plaque measuring fiber-type probe body
802 Connector/light guide
803 GRIN lens
804 Prism
805 Rotation means
806 Sheath

The invention claimed is:

1. A method for measuring and displaying gingiva and/or alveolar bone, the method comprising:
dividing near infrared light output from a light source into measurement light and reference light;
applying the measurement light toward a tooth and periodontal tissue in an oral cavity, and scanning the tooth and the periodontal tissue with the measurement light;
producing interference light from reflected light and backscattered light from the tooth and the periodontal tissue and the reference light;
generating an optical coherence tomographic image based on a scattering intensity value of the interference light;
extracting a gingiva region and/or an alveolar bone region each having a specific scattering intensity value from the optical coherence tomographic image;
quantifying the gingiva and/or the alveolar bone from the extracted gingiva region and/or an alveolar bone region; and
generating an image of the gingiva and/or the alveolar bone,
wherein extracting the gingiva region and/or the alveolar bone region is performed by automatically extracting a portion having predetermined threshold values of the gingiva region and/or the alveolar bone region specified based on the scattering intensity values, which threshold values are distinguished from other periodontal tissues.

2. The method according to claim 1,
wherein the optical coherence tomographic image is a two-dimensional optical coherence tomographic image that two-dimensionally displays the gingiva region, the alveolar bone region, and the other periodontal tissues distinguishably from one another.

3. The method according to claim 1,
wherein the optical coherence tomographic image is a three-dimensional optical coherence tomographic image that three-dimensionally displays, as a stereoscopic image, the gingiva region, the alveolar bone region, and the other periodontal tissues distinguishably from one another.

4. The method according to claim 3,
wherein quantifying the gingiva comprises digitizing a volume of the gingiva based on the gingiva region extracted from the three-dimensional optical coherence tomographic image.

5. The method according to claim 4, wherein the volume of the gingiva is obtained by the following formula:

The volume of gingiva in the real space=$k_a \times 10^9 \times 1/V_a$ ($\mu m^3$/voxel)×the volume (voxels) of the extracted gingiva region×1 /k wherein $V_a$ is a voxel number count corresponding to the volume of an object A actually extracted from the three-dimensional optical coherence tomographic image, the object A having a volume of 1 mm$^3$ in the real space and a refractive index $k_a$; and
k is a refractive index of the gingiva.

6. The method according to claim 3,
wherein quantifying the alveolar bone comprises digitizing a volume of the alveolar bone based on the alveolar bone region extracted from the three-dimensional optical coherence tomographic image.

7. The method according to claim 6, wherein the volume of the alveolar bone is obtained by the following formula:

The volume of alveolar bone in the real space=$k_a \times 10^9 \times 1/V_a$ ($\mu m^3$/voxel)×the volume (voxels) of the extracted alveolar bone region×1 /k wherein $V_a$ is a voxel number count corresponding to the volume of an object A actually extracted from the three-dimensional optical coherence tomographic image, the object A having a volume of 1 mm$^3$ in the real space and a refractive index $k_a$; and
k is a refractive index of the alveolar bone.

8. The method according to claim 1,
wherein the optical coherence tomographic image is a combination of a two-dimensional optical coherence tomographic image that two-dimensionally displays the gingiva region, the alveolar bone region, and the other periodontal tissues distinguishably from one another and a three-dimensional optical coherence tomographic image that three-dimensionally displays, as a stereoscopic image, the gingiva region, the alveolar bone region, and the other periodontal tissues distinguishably from one another.

9. The method according to claim 8,
wherein quantifying the gingiva comprises digitizing a cross-sectional area of the gingiva based on the gingiva region extracted from the two-dimensional optical coherence tomographic image or the three-dimensional optical coherence tomographic image.

10. The method according to claim 9, wherein the cross-sectional area of the gingiva is obtained by the following formula:

The cross-sectional area of gingiva in the real space=$k_a \times 10^6 \times 1/P_{a3}$ ($\mu m^2$/pixels)×the cross-sectional area (pixels) of the extracted gingiva region×1 /k wherein $P_{a3}$ is a pixel number count corresponding to the thickness of an object A actually extracted from the two-dimensional optical coherence tomographic image, the object A having a cross-sectional area of 1 mm$^2$ in the real space and a refractive index $k_a$; and
k is a refractive index of the gingiva.

11. The method according to claim 8,
wherein quantifying the alveolar bone comprises digitizing a cross-sectional area of the alveolar bone based on the alveolar bone region extracted from the two-dimensional optical coherence tomographic image or the three-dimensional optical coherence tomographic image.

12. The method according to claim 11, wherein the cross-sectional area of the alveolar bone is obtained by the following formula:

The cross-sectional area of alveolar bone in the real space=$k_a \times 10^6 \times 1/P_{a3}$ ($\mu m^2$/pixels)×the cross-sectional area (pixels) of the extracted alveolar bone region×1 /k wherein $P_{a3}$ is a pixel number count corresponding to the thickness of an object A actually extracted from the two-dimensional optical coherence tomographic image, the object A having a cross-sectional area of 1 mm$^2$ in the real space and a refractive index $k_a$; and
k is a refractive index of the alveolar bone.

13. The method according to claim 1,
further comprising obtaining an amount of change in swelling of the gingiva and/or an amount of change in the alveolar bone by quantifying gingiva and/or alveolar bone in a time course.

* * * * *